US008399738B2

(12) United States Patent
Stoop et al.

(10) Patent No.: US 8,399,738 B2
(45) Date of Patent: Mar. 19, 2013

(54) FRUCTAN BIOSYNTHETIC ENZYMES

(75) Inventors: Johan M. Stoop, Kennett Square, PA (US); Stephen M. Allen, Wilmington, DE (US); Perry G. Caimi, Kennett Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/435,545

(22) Filed: Mar. 30, 2012

(65) Prior Publication Data

US 2012/0185966 A1 Jul. 19, 2012

Related U.S. Application Data

(60) Division of application No. 13/011,345, filed on Jan. 21, 2011, now Pat. No. 8,168,862, which is a continuation of application No. 11/930,552, filed on Oct. 31, 2007, now Pat. No. 7,875,763, which is a continuation of application No. 11/780,546, filed on Jul. 20, 2007, now Pat. No. 7,803,986, which is a continuation of application No. 10/916,247, filed on Aug. 11, 2004, now Pat. No. 7,253,335, which is a division of application No. 10/003,392, filed on Oct. 30, 2001, now Pat. No. 6,791,015.

(60) Provisional application No. 60/269,543, filed on Feb. 16, 2001, provisional application No. 60/244,273, filed on Oct. 30, 2000.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. ............... 800/284; 800/298; 435/320.1; 435/419; 435/193; 536/23.2; 536/23.6

(58) Field of Classification Search .................. None
See application file for complete search history.

(56) References Cited

U.S. PATENT DOCUMENTS

| 6,057,494 | A * | 5/2000 | Koops et al. ............... 800/284 |
| 6,780,623 | B1 | 8/2004 | Kawakami et al. |
| 2002/0170086 | A1 | 11/2002 | Allen et al. |

FOREIGN PATENT DOCUMENTS

| WO | WO 94/04692 | 3/1994 |
| WO | WO 94/11516 | 5/1994 |
| WO | WO 94/14970 | 7/1994 |
| WO | WO 95/13389 | 5/1995 |
| WO | WO 96/01904 | 1/1996 |
| WO | WO 97/29166 | 8/1997 |
| WO | WO 97/42331 | 11/1997 |
| WO | WO 98/21023 | 7/1998 |
| WO | WO 98/39460 | 9/1998 |
| WO | WO 99/24593 A1 | 5/1999 |
| WO | WO 99/46395 A1 | 9/1999 |
| WO | WO 00/14246 | 3/2000 |

OTHER PUBLICATIONS

Hubert Schweck et al., New Developments in the Use of Sucrose as an industrial Bulk Chemical, Carbohydrates as Organic Raw Matierals, Lichlenlheler ed., VCH Press, NY, pp. 72-82, 1992.
Werner Praznik et al., Inulin Composition during Growth of Tubers of Hellanlhus tuberosus, Agric, Biol. Chem., vol. 51(6):1593-1599, 1987.
Bahman Yazdi-Samadi et al., Components of Developing Soybean Seeds: Oil, Protein, Sugars, Starch, Organic Acids, and Amino Acids, Agronomy Journal, vol. 69:48-466, 1977.
Sari A. Ruuska et al., Contrapunial Networks of Gene Expression during Arabidopsis Seed Filling, The Plant Cell, vol. 14:1191-1206, 2002.
Elke M. Hellwege et al., Transgenic polalo (Solanum tubersum) tubers synthesize the full spectrum of inulin molecules naturally occuring in globe artichoke (Cynara scolymus) roots, PNAS, vol. 97(15):8699-8904, 2000.
U.S. Appl. No. 10/644,335, filed Aug. 20, 2003.
Office Action mailed Jan. 19, 2006, in co-pending U.S. Appl. No. 10/644,335.
Response dated Feb. 20, 2006, to Office Action mailed Jan. 19, 2006, In co-pending U.S. Appl. No. 10/644,335.
Office Action mailed Apr. 17, 2006, in co-pending U.S. Appl. 10/644,335.
Notice of Abandonment mailed Nov. 14, 2006, In co-pending U.S. Appl. 10/644,335.
National Center for Biotechnology information general identifier No. 3367690, Jan. 28, 1999. Van Der Meer, I.M., et al., Cloning of the fructane biosynthesis pathway of jerusalem artichoke.
Ingrid M. Van Der Meer, et al., The Plant Journal, vol. 15:489-500, 1998, Cloning of the Fructane bopsynthesis pathway of Jerusalem artichoke.
Jaeho Cha, et al., Journal of Biotechnology, vol. 91:49-61, 2001, Molecular and Enzymatic characterization of a levan fructotransferase from microbacterium SP. AL-210.
Katsuichi Saito, et al., Biosci. Biotech. Biochem., vol. 61:2076-2079, 1997, Molecular cloning of levan fructotransferase gene from arthrobacter nicotinovorans GS-9 and its expression in *escherichia coli*.
National center for biotechnology information general identifier No. 734567, Jul. 21, 2000, Sprenger, N., et al., Purification, cloning and functional expression of sucrose; Fructan 6-Fructosyltransferase, A key enzyme of fructan synthesis in barley.
National center for biotechnology information general identifier No. 33567711, Jan. 28, 1999, Van Der Meer, I.M. et al., Cloning of the fructane biosynthesis pathway of jerusalem artichoke. Norbert Sprenger et al., PNAS, vol. 92:11653-11658, Dec. 1995, Purification, cloning, and functional expression of sucrose-fructan 6-Fructosyltransferase, A key enzyme of fructan synthesis in barley.

* cited by examiner

*Primary Examiner* — Russell Kallis

(57) ABSTRACT

This invention relates to isolated nucleic acid fragments encoding fructosyltransferases. More specifically, this invention relates to polynucleotides encoding 1-FFTs, 6-SFTs, or 1-SSTs. The invention also relates to the construction of a recombinant DNA constructs encoding all or a portion of the fructosyltransferases, in sense or antisense orientation, wherein expression of the recombinant DNA construct results in production of altered levels of the fructosyltransferases in a transformed host cell.

11 Claims, 8 Drawing Sheets

```
                  *  *  *     ***     *    *        *    *     *   *
SEQ ID NO:17      MQTPE-PFTDLEHEPH---TPLLDHHHNPPQTTT----KPLFTRVVSGVTFVLFPFGFA
SEQ ID NO: 2      MTTT-KPFSDLED------APLLNHTEPPPPPPTAGRKRLLIKVVSVITLLILLIV-S
SEQ ID NO: 4      MTTPEQPITDLEHEPNHNRTPLLDHNESQPVK------KHLFFKVLSGVTFISLFFISA
SEQ ID NO: 6      ------------------------------------------------------------
                  1                                                          60

***   ***  *   ******************    *   **
SEQ ID NO:17      IVFIVLNQQNSSVRIVTNSEKSFIRYSQTDRLSWERTAFHFQPAKNFIYDPDGQLFHMGW
SEQ ID NO: 2      VLF--LNQQNSS----HSTTNSKSISQSDRLIWERTSFHFQPAKNFIYDPNGPLFHMGW
SEQ ID NO: 4      FLFIVLNQQNST----NISVKYSQSDRLTWERTAFHFQPAKNFIYDPNGQMYYMGW
SEQ ID NO: 6      ------------------------------------------------------------
                  61                                                         120

**  *********  *****************  ******  ******  ******
SEQ ID NO:17      YHMFYQYNPYAPVWGNMSWGHSVSKDMINWYELPVAMVPTEWYDIEGVLSGSTTVLPNGQ
SEQ ID NO: 2      YHLFYQYNPYGPVWGNMSWGHSVSKDMINWFELPVALVPTEWYDIEGVLSGSTTVLPNGQ
SEQ ID NO: 4      YHLFYQYNPYAPVWGNMSWGHSVSKDMINWYELPVAIVPTEWYDIEGVLSGSITVLPNGQ
SEQ ID NO: 6      ------------------------------------------------------------
                  121                                                        180

*****************   ******   ******************  ******
SEQ ID NO:17      IFALYTGNANDFSQIQCKAVPVNLSDPLLIEWVKYEDNPILYTPPGIGLKDYRDPSTVWT
SEQ ID NO: 2      IFALYTGNANDFSQLQCKAVPVNISDPLLIEWVKYDGNPILYTPPGIGLKDYRDPSTVWT
SEQ ID NO: 4      IFALYTGNANDFSQLQCKAVPVNSSDPLLVEWVKYEDNPILYTPPGIGLKDYRDPSTVWT
SEQ ID NO: 6      ----------------------------------------------TR--STVWT
                  181                                                        240
```

FIG. 1A

```
SEQ ID NO:17   ************ ** *** *** ** ************************
SEQ ID NO: 2   GPDGKHRMIMGTKRGNTGMVLVYTTDYTNYELLDEPLHSVPNTDMWECVDFYPVSLTND
SEQ ID NO: 4   GPDGKHRMIMGSKRNKTGLVLVYHTTDFTNYVMSDEPLHSVPNTDMWECVDFYPVSLTND
SEQ ID NO: 6   GPDGKHRMIMGTKRGNTGMILVYHTTDYTNYEMLNEPMHSVPNTDMWECVDFYPVSLTND
               GPDGKHRMIMGSKRGNTGMILVYHTTDYTNYELLDEPLHSVPNTDMWECVDFYPVSLTND
                                                                        300
                                                                        241

SEQ ID NO:17   **** *************** ** *** ***  ************ * ********
SEQ ID NO: 2   SALDMAAYGSGIKHVIKESWEGHGMDWYSIGTYDAINDKWTPDNPELDVGIGLRCDYGRF
SEQ ID NO: 4   SALDMAAYGSGIKHVIKESWEGHGMDWYSIGTYDASTDKWTPDNPKLDVGIGLRCDYGKF
SEQ ID NO: 6   SALDIAAYGSGIKHVIKESWEGYGMDFYSIGTYDAFNDKWTPDNPELDVGIGLRCDYGRF
               SALDMAAYGSGIKHVIKESWEGHGMDWYSIGTYDAINDKWTPDNPELDVGIGLRCDYGKF
                                                                        360
                                                                        301

SEQ ID NO:17   ******* * ******* ** *** ***************  ***************
SEQ ID NO: 2   FASKSLYDPLKKRRITWGYVGESDSADQDLSRGWATVYNVGRTIVLDRKTGTHLLHWPVE
SEQ ID NO: 4   FASKSLFDPLKKRRVTWGYVGESDKPDQDLSRGWATIYNVARTVVLDRKTGTHLLHWPVE
SEQ ID NO: 6   FASKSIFDPVKKRRITWAYVGESDNADDDLSRGWATIYNVGRTIVLDRKTGTHLLHWPVE
               FASKSLYDPLKKRRVTWAYVGESDSVDQDLSRGWATVYNVGRTIVLDRKTGTHLLHWPVE
                                                                        420
                                                                        361

SEQ ID NO:17   * **** * *** ******* *** **** **** * * *** ***           **
SEQ ID NO: 2   EVESLRYNGQEFKEIKLEPGSIIPLDIGTATQLDIVATFEVDQAALNATSETDDIYGCTT
SEQ ID NO: 4   EIESLRSNGQEFNEIELKPGSIIPLDIGSATQLDIVATFEVDQDALKAISETNEEYICTK
SEQ ID NO: 6   EIESLRYNGQEFKEIKLEPGSIAPLDIGTATQLDIVATFKVDEAALNATSETDDNFACTT
               EVESLRYNGQEFKEIELEPGSIIPLDIGTATQLDIVATFEVDQAALNATSETDDIYGCTT
                                                                        480
                                                                        421
```

FIG. 1B

```
                    *  *  *********** **  ****************************  **  * ********* *
SEQ ID NO:17        SLGAAQRGSLGPFGLAVLADGTLSELTPVYFYFYIAKKADGGVSTHFCTDKLRSSLDYDGER
SEQ ID NO: 2        SWGAAGRGSLGPFGVAVLADGTLSELTPVYFYFYIAKNTDGSVATHFCTDKLRSSLDYDRER
SEQ ID NO: 4        SSGAVERGSLGPFGLAVIADGTLSELTPVYFYFYIAKKADGGVSTHFCTDKLRSSLDFDKER
SEQ ID NO: 6        SLGAAQRGSLGPFGLAVLADGTLSELTPVYFYFYIAKKADGGLSTHFCTDKLRSSLDYDGQR
                    481                                                          540

****  ******* *  ***************  ****  ********  **  *******
SEQ ID NO:17        VVYGGTVPVLDDEELTMRLLVDHSIVEGFAQGGRTVITSRAYPTKAIYEQAKLFLFNNAT
SEQ ID NO: 2        VVYGSTVPVLDGEELTMRLLVDHSVVEGFAQGGRTVITSRVITSRVYPTKAIYDNAKVFLFNNAT
SEQ ID NO: 4        VVYGSTVPVLDDEELTMRLLVDHSVVEEAFAQGGRIAITSRVYPTKAIYEGAKLFLFNNAT
SEQ ID NO: 6        VVYGSTVPVLDDEELTMRLLVDHSIVEGFAQGGRTVITSRVYPTKAIYEQAKLFLFNNAT
                    541                                                          600

************ *  *
SEQ ID NO:17        GTSVKASLKIWQMASAPIHQYPF-
SEQ ID NO: 2        GTSVKASLKIWQMAPAQIKPYPL-
SEQ ID NO: 4        DTSVKASLKIWQMASAQIHQYEFN
SEQ ID NO: 6        GTSVKASLKIWQMASAQIHQYSF-
                    601                    624
```

FIG. 1C

```
                           *  *                                             ***
SEQ ID NO:21    MGSHGKPPLPPYAYKPLPSDAADGKRTGCMRWSACATVLTASAMAVVVGATLLAGLRMEQ
SEQ ID NO: 8    ------------------------------------------------------------
SEQ ID NO:10    ------------------------------------------------------------
SEQ ID NO:12    ------------------------------------------------------------
SEQ ID NO:20    MASESSRR--------GDSTSTRR------RSGQEPLAVLVSAKNQSSEERAGGGLRV--
                1                                                           60

********** *****       *  ******************
SEQ ID NO:21    AVDEEAAAGGFPWSNEMLQWRSGYHFQTAKNYMSDPNGLMYYRGWYHMFYQYNPVGTDW
SEQ ID NO: 8    ------------------------------------------------------------
SEQ ID NO:10    ------------------------------------------------------------
SEQ ID NO:12    ------------------------------------------------------------
SEQ ID NO:20    ---DEEAAAG--FPWSNEMLQWRSGYHFQTAKNYMSDPNGLMYYNGWYHMFFQYNPVGTDW
                61                                                         120

***   ******     **  ****************** **********************
SEQ ID NO:21    DDGMEWGHAVSRNLVQWRTLPIAMVADQWYDILGVLSGSMTVLPNGTVIMIYTGATNASA
SEQ ID NO: 8    ---TRWGHAVSRNLVTWRTLPIAMVADQWYDILGVLSGSMTVLPNGTVIMIYTGATNASA
SEQ ID NO:10    ---ARD------------------DILGVLSGSMTVLPNGTVIMIYTGATNASA
SEQ ID NO:12    ------------------------------------------------------------
SEQ ID NO:20    DDGMEWGHAVSRNLVTWRTLPIAMVADQWYDILGVLSGSMTVLPNGTVIMIYTGATNASA
                121                                                        180

*********************  ***********************************
SEQ ID NO:21    VEVQCIATPADPNDPLLRRWTKHPANPVIWSPPGVGTKDFRDPMTAWYDESDETWRTLLG
SEQ ID NO: 8    IEVQCIATPADPNDPFLRRWTKHPANPVIWSPPGIGTKDFRDPMTAWYDESDDTWRTLLG
SEQ ID NO:10    VEVQCIATPADPNDPFLRRWTKHPANPVIWSPPGIGTKDFRDPMTAWYDESDDTWRTLLG
SEQ ID NO:12    ------------------------------------------------------------
SEQ ID NO:20    VEVQCIATPADPNDPFLRRWTKHPANPVIWSPPGIGTKDFRDPMTAWYDESDDTWRTLLG
                181                                                        240
```

FIG. 2A

```
SEQ ID NO:21    ****  ******************************  **  *********************
SEQ ID NO:8           SKDDHDGHHDGIAMMYKTKDFLNYELIPGILHRVVRTGEWECIDFYPVGRRSSDNSSEML
SEQ ID NO:10          SKDDQDGHHDGIAMMYKTKDFLNYELIPGILHRVERTGEWFCIDFYPVGRRSSDNSSEML
SEQ ID NO:12          SKDDHDGHHDGIAMMYKTKDFLNYELIPGILHRVQRTGEWECIDFYPVGHRSNDNSSEML
SEQ ID NO:20          ------------------------------------------------------------
                      SKDDHDGHHDGIAMMYKTKDFLNYELIPGILHRVQRTGEWECIDFYPVGHRSNDNSSEML
                    241                                                      300

SEQ ID NO:21    ****  **********************************  **  ****************
SEQ ID NO:8           HVLKASMDDERHDYYSLGTYDSAANTWTPIDPELDLGIGLRYDWGKFYASTSFYDPAKNR
SEQ ID NO:10          HVLKASMDDERHDYYSLGTYDSAANTWTPIDPDLDLGIGLRYDWGKFYASTSFYDPAKKR
SEQ ID NO:12          HVLKASMDDERHDYYSLGTYDSAANAWTPIDPELDLGIGLRYDWGKFYASTSFYDPAKKR
SEQ ID NO:20          ------------------------------------------------------------
                      HVLKASMDDERHDYYSLGTYDSAANAWTPIDPELDLGIGLRYDWGKFYASTSFYDPAKKR
                    301                                                      360

SEQ ID NO:21    ***   *****************************  *  *********************
SEQ ID NO:8           RVLMGYVGEVDSKRADVVKGWASIQSVPRTVALDEKTRTNLLLWPVEEIETLRLNATELT
SEQ ID NO:10          RVLMGYVGEVDSKRADVVKGWASIQSVPRTIALDEKTRTNLLLWPVEEIETLRLNATELS
SEQ ID NO:12          RVLMGYVGEVDSKRADVVKGWASIQSVPRTIALDEKTRTNLLLWPVEEIETLRLNATELS
SEQ ID NO:20          ------------------------------------------------------------
                      RVLMGYVGEVDSKRADVVKGWASIQSVPRTIALDEKTRTNLLLWPVEEIETLRLNATELS
                    361                                                      420

SEQ ID NO:21    ***   **************************  *********  ****************
SEQ ID NO:8           DVTINTGSVIHIPLRQGTQLDIEASFHLDASAVAALNEADVGYNCSSSGGAVNRGALGPF
SEQ ID NO:10          DVTMNTGSVIHIPLRQGTQLDIEATFHLDASAVAALNEADVGYNCSSSGGAVNRGALGPF
SEQ ID NO:12          DVTLNTGSVIHIPLRQGTQLDIEATFHLDASAVAALNEADVGYNCSSSGGAVNRGALGPF
SEQ ID NO:20          ------------------------------------------------------------
                      DVTLNTGSVIHIPLRQGTQLDIEATFHLDASAVAALNEADVGYNCSSSGGAVNRGALGPF
                    421                                                      480
```

FIG. 2B

```
SEQ ID NO:21    *************  GLLVLAAGDRRGEQTAVYFYVSRGLDGGLHTSFCQDELRSSRAKDVTKRVIGSTVPVLDG
SEQ ID NO: 8                   GLLVLAAGDRRGEQTAVYFYVSRGLDGGLHTSFCQDELRSSRAKDVTKRVIGSTVPVLDG
SEQ ID NO:10                   GLLVLAAGDRRGEQTAVYFYVSRGLDGGLHTSFCQDELRSSRAKDVTKRVIGSTVPVLDG
SEQ ID NO:12                   ------------------------------------------------------------
SEQ ID NO:20                   GLLVLAAGDRRGEQTAVYFYVSRGLDGGLHTSFCQDELRSSRAKDVTKRVIGSTVPVLDG
                481                                                                 540

SEQ ID NO:21    ** ************* ** *************  EALSMRVLVDHSIVQGFDMGGRTTMTSRVYPMESYQEARVYLFNNATGASVTAERLVVHE
SEQ ID NO: 8                                       EAFSMRVLVDHSIVQGFAMGGRTTMTSRVYPMEAYQEAKVYLFNNATGASVMAERLVVHE
SEQ ID NO:10                                       EAFSMRVLVDHSIVQGFAMGGRTTMTSRVYPMEAYQEAKVYLFNNATGASVMAERLVVHE
SEQ ID NO:12                                       ------ARATMTSRVYPMEAYQEAKVYLFNNATGASVTAERLVVHE
SEQ ID NO:20                                       EAFSMRVLVDHSIVQGFAMGGRTTMTSRVYPMEAYQEAKVYLFNNATGASVMAERLVVHE
                541                                                                 600

SEQ ID NO:21    ************ **   MDSAHNQLSNEDDGMYLIQVLESRH
SEQ ID NO: 8                      MDSAHNQLSNMDDYSYVQ-------
SEQ ID NO:10                      MDSAHNQLSNMDDHSYVQ-------
SEQ ID NO:12                      MDSAHNQLSNMDDYSYVQ-------
SEQ ID NO:20                      MDSAHNQLSNMDDHSYVQ-------
                601                        625
```

FIG. 2C

```
SEQ ID NO:18        MMASSTTTPLILHDDPENLPELTGSPTTRRLSIAKVLSGILVSVLVIGALVALINNQTYESP------
SEQ ID NO:14        MMASSTTTSPLILHDDPENLQEPTGFTGVRRPSIAKALCVTLVSVMVICGLVAVISNQTQVPQVANSHQG
SEQ ID NO:16        MMASSTTTPLILHDDPENLPELTGSPTTRRLSIAKVLSGILVSVLVTCALVALINNQTYEPP------
                    1                                                                  70

SEQ ID NO:18        SATTFVTQLPNIDLKRVPGKLDSSAEVEWQRSTYHFQPDKNFISDPDGPMYHMGWYHLFYQYNFQSAIWG
SEQ ID NO:14        AATTFTTQLPKIDMKRVPGELDSGADVQWQRSAYHFQPDKNYISDPDGPMYHMGWYHLFYQYNPESAIWG
SEQ ID NO:16        AATTFATQLPNIDLKRVPGKLDSSAEVEWQRSAYHFQPDKNFISDPDGPMYHMGWYHLFYQYNPESAIWG
                    61                                                                  140

SEQ ID NO:18        NITWGHSVSKDMINWFHLPFAMVPDHWYDIEGVMTGSATVLPNGQIIMLYSGNAYDLSQVQCLAYAVNSS
SEQ ID NO:14        NITWGHSVSKDMINWFHLPFAMVPDHWYDIEGVMTGSATVLPNGEIIMLYTGNAYDLSQVQCLAYAVNSS
SEQ ID NO:16        NITWGHSVSKDMINWFHLPFAMVPDHWYDIEGVMTGSATVLPNGQIIMLYTGNAYDLSQVQCLAYAVNSS
                    141                                                                 210

SEQ ID NO:18        DPLLIEWKKYEGNPVLLPPGVGYKDFRDPSTLWSGPDGEYRMVGSKINETIGCALIYHTTNFTHFELK
SEQ ID NO:14        DPLLIEWKKYEGNPVLLPPPGVGYKDFRDPSTLWLGPDGEYRMVGSKINETIGCALIYHTTNFTHFELN
SEQ ID NO:16        DPLLIEWKKYEGNPVLFPPGVGYKDFRDPSTLWLGPDGEYRMVGSKINETIGCALIYHTTNFTHFELK
                    211                                                                 280

SEQ ID NO:18        EEVLHAVPHTGMWECVDLYPVSTVHTNGLDMVDNGPNVKYVLKQSGDEDRHDWYAIGSYDIVNDKWYPDD
SEQ ID NO:14        EEVLHAVPHTGMWECVDLYPVSTTHTNGLDMVDNGPNVKYVILKQSGDEDRHDWYAIGSYDWVNDKWYPDD
SEQ ID NO:16        EEVLHAVPHTGMWECVDLYPVSTVHTNGLDMVDNGPNVKYVLKQSGDEDRHDWYAIGSYDVVNDKWYPDD
                    281                                                                 350
```

FIG. 3A

```
                   ******************* *** ********************
SEQ ID NO:18       PENDVGIGLRYDFGKFYASKTFYDQHKKRRVLWGYVGETDPQKYDLSKGWANILNIPRTVVLDLETKTNLIQ
SEQ ID NO:14       PENDVGIGLRYDYGKFYASKTFYDQHKKRRVLWGYVGETDPEKYDLTKGWANILNIPRTVLDTKTKTNLIQ
SEQ ID NO:16       PENDVGIGLRYDFGKFYASKTFYDQHKKRRVLWGYVGETDPQKYDISKGWANILNIPRTVVLDTKTKTNLIQ
                   351                                                                    422

****** ****** ** * ************ *** ********************  ***  ********
SEQ ID NO:18       WPIEETENLRSKKYDEFKDVELRPGALVPLEIGTATQLDIVATFEIDQKMLESTLEADVLFNCTTSEGSVAR
SEQ ID NO:14       WPIEETEKLRSKKYDKFVDVELRPGSLIPLEIGTATQLDIVATFEVDQMMLESTLEADVLFNCTTSVGSVGR
SEQ ID NO:16       WPIEETENLRSKTYDEFKDVELRPGSLVPLEIGTATQLDIVATFEIDQKMLESTLEADVLFNCTTSEGSVAR
                   423                                                                    494

****** ************** ******* ****************************** ********
SEQ ID NO:18       SVLGPFGVVVLADAQRSEQLPVYFYIAKDIDGTSRTYFCADETRSSKDVSVGKWVYGSSVPVLPGEKYNMRL
SEQ ID NO:14       GVLGPFGVVVLADAQRTEQLPVYFYIAKDTDGTSRTYFCADETRSSKDVDVGKWVYGSSVPVLPNEKYNMRL
SEQ ID NO:16       GALGPFGVVVLADAQRSEQLPVYFYIAKDIDGTSRTYFCADETRSSKDVSVGKWVYGSSVPVLPGEKYNMRL
                   495                                                                    566

****************************************** ***** *****   ***  ********
SEQ ID NO:18       LVDHSIVEGFAQNGRTVVTSRVYPTKAIYNAATGISVKASIKIWKMGEAELNPFPLPGWTFEL
SEQ ID NO:14       LVDHSIVEGFAQNGRTVVTSRVYPTKAIYNAAKVFLFNNATGIRVKASVKIWKMAEAELNPFPVTGWTS--
SEQ ID NO:16       LVDHSIVEGFAQNGRTVVTSRVYPTKAIYNAAKVFLFNNATGISVKASIKIWKMAKAELNPFPLPGWTFEL
                   564                                                                    637
```

FIG. 3B

SEQUENCE LISTING

<160> NUMBER OF SEQ ID NOS: 21

<210> SEQ ID NO 1
<211> LENGTH: 2080
<212> TYPE: DNA

-continued

<213> ORGANISM: Dimorphotheca sinuata

<400> SEQUENCE: 1

| | | | | | |
|---|---|---|---|---|---|
| gcacgagctt | aatcagccca | ttttcctcca | ccatgacaac | caccaaaccc | tttagtgacc | 60 |
| ttgaggacgc | acccctactg | aaccacaccg | aaccaccacc | accaccgcca | ccgccaactg | 120 |
| ccggaagaaa | acggttgttg | atcaaggttg | tgtcagttat | caccctactc | attttgctta | 180 |
| ttgtttcagt | tttgtttctc | aaccaacaaa | attcaagtca | ctccaccacc | aattcaaaat | 240 |
| cgatctccca | atccgatcgc | tcatttggg | aaagaacatc | tttccatttt | caacccgcca | 300 |
| aaaatttcat | ttacgatccc | aatgggccat | tatttcacat | gggttggtac | catcttttct | 360 |
| atcaatacaa | cccgtacggt | cctgtttggg | gaaatatgtc | atggggtcac | tccgttttca | 420 |
| aagacatgat | caactggttt | gagcttccag | tcgcattggt | cccaaccgaa | tggtacgata | 480 |
| tcgagggtgt | tttatccggg | tccaccaccg | tcctccccaa | cggtcaaatc | ttcgcattgt | 540 |
| acacaggaaa | cgctaacgat | ttctcccaat | tacaatgcaa | agctgtaccc | gtcaacatat | 600 |
| ctgacccact | tcttatcgag | tgggtcaaat | acgatggtaa | cccaatcctg | tatactccac | 660 |
| cagggattgg | gttaaaagac | tatcgggacc | cgtcaacagt | ctggacgggt | cccgatggaa | 720 |
| aacatcggat | gatcatggga | tctaaacgaa | acaaaacggg | actagtactt | gtttaccaca | 780 |
| caaccgattt | cacaaattat | gtgatgtcgg | atgagccgtt | gcattcggta | cctaataccg | 840 |
| atatgtggga | atgcgttgac | ttttaccctg | tttcgttgac | caatgatagc | gcgcttgata | 900 |
| tggcggctta | tgggtcgggt | atcaaacacg | tgattaaaga | aagttgggag | ggacatggaa | 960 |
| tggattggta | ttcgattggg | acttatgatg | catcaaccga | taaatggact | ccggataacc | 1020 |
| cgaaattaga | tgtgggtatc | gggttgcgat | gtgattacgg | aaagtttttt | gcatcgaaga | 1080 |
| gtcttttcga | tccgttgaag | aaaaggaggg | tgacttgggg | ttatgttggg | gaatcagata | 1140 |
| aacctgatca | ggacctctct | agaggatggg | ctaccattta | taatgttgca | cggacggtgg | 1200 |
| tactagatag | aaagaccgga | acacatctac | ttcattggcc | agttgaagaa | atcgagagtt | 1260 |
| tgagatccaa | tggtcaagaa | ttcaacgaga | ttgaactcaa | accgggttcg | atcattccac | 1320 |
| ttgacatagg | ctcggctact | cagttggaca | tagttgcgac | atttgaagtg | atcaagatg | 1380 |
| cgttgaaagc | tataagtgaa | accaacgaag | aatatatttg | taccaaaagc | tggggtgcag | 1440 |
| ccggaagggg | aagtttggga | ccatttgggg | ttgcggtttt | agccgatgga | acactttcag | 1500 |
| agttaactcc | cgtgtatttc | tacatagcta | aaaatacgga | tggaagtgta | gcaacacatt | 1560 |
| tttgtaccga | taagctaaga | tcatcactag | attatgatcg | tgaaagagtg | gtgtatggaa | 1620 |
| gcactgtccc | tgtgcttgat | ggtgaagaac | tcacaatgag | gttattggtg | gaccattcgg | 1680 |
| tagtagaagg | gtttgcgcaa | ggaggaagga | cggtaataac | atcaagggtc | tatccgacaa | 1740 |
| aggcaatata | cgacaacgcg | aaggtgttct | tattcaacaa | cgctactggt | acgagtgtga | 1800 |
| aggcgtctct | caagatttgg | caaatggctc | ctgcccagat | taaaccttac | cctctttaat | 1860 |
| catatgtttc | atttcactct | cactagaaca | cttgctgtta | ctattattgt | atcttatatt | 1920 |
| ttttatatgt | acgtaataat | taccgtttgg | atggtttgt | tttgttcaac | ctctgcattg | 1980 |
| tgtgttaagt | agtaagccgc | gattattta | ataatatgaa | taggttgttt | tgttcaaaaa | 2040 |
| aaaaaaaaaa | aaaaaaaaaa | aaaaaaaaaa | aaaaaaaaaa | | | 2080 |

<210> SEQ ID NO 2
<211> LENGTH: 608
<212> TYPE: PRT
<213> ORGANISM: Dimorphotheca sinuata

<400> SEQUENCE: 2

```
Met Thr Thr Thr Lys Pro Phe Ser Asp Leu Glu Asp Ala Pro Leu Leu
  1               5                  10                  15
Asn His Thr Glu Pro Pro Pro Pro Pro Pro Pro Thr Ala Gly Arg
             20                  25                  30
Lys Arg Leu Leu Ile Lys Val Val Ser Val Ile Thr Leu Leu Ile Leu
             35                  40                  45
Leu Ile Val Ser Val Leu Phe Leu Asn Gln Gln Asn Ser Ser His Ser
     50                  55                  60
Thr Thr Asn Ser Lys Ser Ile Ser Gln Ser Asp Arg Leu Ile Trp Glu
 65                  70                  75                  80
Arg Thr Ser Phe His Phe Gln Pro Ala Lys Asn Phe Ile Tyr Asp Pro
                 85                  90                  95
Asn Gly Pro Leu Phe His Met Gly Trp Tyr His Leu Phe Tyr Gln Tyr
            100                 105                 110
Asn Pro Tyr Gly Pro Val Trp Gly Asn Met Ser Trp Gly His Ser Val
            115                 120                 125
Ser Lys Asp Met Ile Asn Trp Phe Glu Leu Pro Val Ala Leu Val Pro
        130                 135                 140
Thr Glu Trp Tyr Asp Ile Glu Gly Val Leu Ser Gly Ser Thr Thr Val
145                 150                 155                 160
Leu Pro Asn Gly Gln Ile Phe Ala Leu Tyr Thr Gly Asn Ala Asn Asp
                165                 170                 175
Phe Ser Gln Leu Gln Cys Lys Ala Val Pro Val Asn Ile Ser Asp Pro
            180                 185                 190
Leu Leu Ile Glu Trp Val Lys Tyr Asp Gly Asn Pro Ile Leu Tyr Thr
        195                 200                 205
Pro Pro Gly Ile Gly Leu Lys Asp Tyr Arg Asp Pro Ser Thr Val Trp
    210                 215                 220
Thr Gly Pro Asp Gly Lys His Arg Met Ile Met Gly Ser Lys Arg Asn
225                 230                 235                 240
Lys Thr Gly Leu Val Leu Val Tyr His Thr Thr Asp Phe Thr Asn Tyr
                245                 250                 255
Val Met Ser Asp Glu Pro Leu His Ser Val Pro Asn Thr Asp Met Trp
            260                 265                 270
Glu Cys Val Asp Phe Tyr Pro Val Ser Leu Thr Asn Asp Ser Ala Leu
        275                 280                 285
Asp Met Ala Ala Tyr Gly Ser Gly Ile Lys His Val Ile Lys Glu Ser
    290                 295                 300
Trp Glu Gly His Gly Met Asp Trp Tyr Ser Ile Gly Thr Tyr Asp Ala
305                 310                 315                 320
Ser Thr Asp Lys Trp Thr Pro Asp Asn Pro Lys Leu Asp Val Gly Ile
                325                 330                 335
Gly Leu Arg Cys Asp Tyr Gly Lys Phe Phe Ala Ser Lys Ser Leu Phe
            340                 345                 350
Asp Pro Leu Lys Lys Arg Arg Val Thr Trp Gly Tyr Val Gly Glu Ser
        355                 360                 365
Asp Lys Pro Asp Gln Asp Leu Ser Arg Gly Trp Ala Thr Ile Tyr Asn
    370                 375                 380
Val Ala Arg Thr Val Val Leu Asp Arg Lys Thr Gly Thr His Leu Leu
385                 390                 395                 400
His Trp Pro Val Glu Glu Ile Glu Ser Leu Arg Ser Asn Gly Gln Glu
                405                 410                 415
```

```
Phe Asn Glu Ile Glu Leu Lys Pro Gly Ser Ile Ile Pro Leu Asp Ile
            420                 425                 430

Gly Ser Ala Thr Gln Leu Asp Ile Val Ala Thr Phe Glu Val Asp Gln
                435                 440                 445

Asp Ala Leu Lys Ala Ile Ser Glu Thr Asn Glu Tyr Ile Cys Thr
450                 455                 460

Lys Ser Trp Gly Ala Ala Gly Arg Gly Ser Leu Gly Pro Phe Gly Val
465                 470                 475                 480

Ala Val Leu Ala Asp Gly Thr Leu Ser Glu Leu Thr Pro Val Tyr Phe
                485                 490                 495

Tyr Ile Ala Lys Asn Thr Asp Gly Ser Val Ala Thr His Phe Cys Thr
                500                 505                 510

Asp Lys Leu Arg Ser Ser Leu Asp Tyr Asp Arg Glu Arg Val Val Tyr
                515                 520                 525

Gly Ser Thr Val Pro Val Leu Asp Gly Glu Glu Leu Thr Met Arg Leu
530                 535                 540

Leu Val Asp His Ser Val Val Glu Gly Phe Ala Gln Gly Gly Arg Thr
545                 550                 555                 560

Val Ile Thr Ser Arg Val Tyr Pro Thr Lys Ala Ile Tyr Asp Asn Ala
                565                 570                 575

Lys Val Phe Leu Phe Asn Asn Ala Thr Gly Thr Ser Val Lys Ala Ser
                580                 585                 590

Leu Lys Ile Trp Gln Met Ala Pro Ala Gln Ile Lys Pro Tyr Pro Leu
                595                 600                 605

<210> SEQ ID NO 3
<211> LENGTH: 2146
<212> TYPE: DNA
<213> ORGANISM: Parthenium argentatum Grey

<400> SEQUENCE: 3
gcacgaggag accagtcagc acacagtaac tgaactcact caacccatta ttcaccttca      60
ccatgacaac ccctgaacaa cccattacag accttgaaca cgaacccaac cacaaccgca     120 caccctatt ggaccacaac gaatcacaac ccgtaaagaa acatttgttc ttcaaagttc     180
tgtctggtgt taccttcatt tcattgttct ttatttctgc tttttttattc attgttttga     240 accaacaaaa ttctaccaat atatcggtta agtactcgca atccgatcgc ttacgtggg     300 aacgaaccgc ttttcatttt caaccggcca agaatttat ttatgatccc aatggtcaaa     360
tgtactacat gggctggtac catctattct atcaatacaa tccatacgca ccggtttggg     420
gtaatatgtc atggggtcac tccgtatcca agacatgat caactggtac gagctacccg     480
tcgctatagt cccgactgaa tggtatgata ttgagggcgt cttatctggg tccatcacag     540
tgcttcccaa cgggcagatc tttgcattgt acacggggaa tgctaatgac tttcccaat     600 tgcaatgcaa agctgtaccc gtgaactcat ctgacccact tcttgttgag tgggtcaagt     660
acgaagataa cccaatcctg tacactccac cagggattgg gttaaaagac tatagggacc     720
cgtcaacagt ctggacgggt cctgatgaa agcataggat gatcatggga actaaacgtg     780
gcaatacagg aatgatactt gtttaccata ccactgatta cacgaactat gagatgttga     840
atgagcctat gcactcggtt cccaataccg atatgtggga atgcgttgac ttttacccgg     900
tttcattaac caacgatagt gcacttgata ttgcggccta cgggtcgggt atcaaacacg     960
tgattaaaga aagttgggag ggatatggga tggattcta ttcaatcggg acttatgacg    1020
catttaacga taaatggact cccgataacc cagagttaga tgttggtatc gggttgcggt    1080
```

```
gtgattacgg taggttttt gcatcaaaga gtatttttga cccagtgaag aaaaggagga    1140
tcacttgggc ttatgttgga gaatcagata atgctgatga tgacctctcc agaggatggg    1200
ctactattta taatgttgga agaactattg tactagatag aaagaccggg acccatttac    1260
ttcattggcc tgtcgaggaa atcgagagtt tgagatacaa tggtcaggaa tttaaagaga    1320
tcaaactaga gcccggttca attgctccac tcgacatagg caccgctaca cagttggaca    1380
tagttgcaac atttaaggtg gatgaggctg cattgaacgc gacaagtgaa accgatgata    1440
acttcgcttg caccacgagc tcaggtgcag ttgaagggg aagtttggga ccatttggtc    1500
ttgcggttct agctgatgga acccttccg agtaactcc ggtttatttc tacattgcta    1560
aaaaggccga tggaggtgtg tcaacacatt tttgtaccga taagctaagg tcatccttgg    1620
attttgataa ggagagagtg gtgtacggta gcactgttcc tgtgttagat gatgaagaac    1680
tcacaatgag gctattggtg gatcattcgg tagtcgaggc gtttgcacaa ggaggaagga    1740
ttgccataac atcaagggtg tatccgacga aagcaatata cgaaggagcg aagttgttct    1800
tattcaacaa tgccacggat acgagtgtga aggcatctct caagatttgg caaatggctt    1860
ctgcccaaat tcatcaatac gagtttaatt aggggctctc gttatcctta ttattagtat    1920
ttatgtattt taatttattt agacctatgt atttgatcat atgagttctt atcgtgcttt    1980
aagtagtaaa tgaattgtgt ttgggtaaaa aataaaaaa aaaaaaaaa aaaaaaaaa    2040 aaaaaaaaa aaaaaaaaa aaaaaaaaa aaaaaaaaa aaaaaaaaa aacaaaaaaa    2100 gaaaaaaaa aaaaaaaaa aaaaaaaaa aaaaaaaaa aaaaaa    2146
```

```
<210> SEQ ID NO 4
<211> LENGTH: 609
<212> TYPE: PRT
<213> ORGANISM: Parthenium argentatum Grey

<400> SEQUENCE: 4

Met Thr Thr Pro Glu Gln Pro Ile Thr Asp Leu Glu His Glu Pro Asn
  1               5                  10                  15

His Asn Arg Thr Pro Leu Leu Asp His Asn Glu Ser Gln Pro Val Lys
             20                  25                  30

Lys His Leu Phe Phe Lys Val Leu Ser Gly Val Thr Phe Ile Ser Leu
         35                  40                  45

Phe Phe Ile Ser Ala Phe Leu Phe Ile Val Leu Asn Gln Gln Asn Ser
     50                  55                  60

Thr Asn Ile Ser Val Lys Tyr Ser Gln Ser Asp Arg Leu Thr Trp Glu
 65                  70                  75                  80

Arg Thr Ala Phe His Phe Gln Pro Ala Lys Asn Phe Ile Tyr Asp Pro
                 85                  90                  95

Asn Gly Gln Met Tyr Tyr Met Gly Trp Tyr His Leu Phe Tyr Gln Tyr
            100                 105                 110

Asn Pro Tyr Ala Pro Val Trp Gly Asn Met Ser Trp Gly His Ser Val
        115                 120                 125

Ser Lys Asp Met Ile Asn Trp Tyr Glu Leu Pro Val Ala Ile Val Pro
    130                 135                 140

Thr Glu Trp Tyr Asp Ile Glu Gly Val Leu Ser Gly Ser Ile Thr Val
145                 150                 155                 160

Leu Pro Asn Gly Gln Ile Phe Ala Leu Tyr Thr Gly Asn Ala Asn Asp
                165                 170                 175

Phe Ser Gln Leu Gln Cys Lys Ala Val Pro Val Asn Ser Ser Asp Pro
            180                 185                 190
```

```
Leu Leu Val Glu Trp Val Lys Tyr Glu Asp Asn Pro Ile Leu Tyr Thr
            195                 200                 205

Pro Pro Gly Ile Gly Leu Lys Asp Tyr Arg Asp Pro Ser Thr Val Trp
        210                 215                 220

Thr Gly Pro Asp Gly Lys His Arg Met Ile Met Gly Thr Lys Arg Gly
225                 230                 235                 240

Asn Thr Gly Met Ile Leu Val Tyr His Thr Asp Tyr Thr Asn Tyr
                245                 250                 255

Glu Met Leu Asn Glu Pro Met His Ser Val Pro Asn Thr Asp Met Trp
                260                 265                 270

Glu Cys Val Asp Phe Tyr Pro Val Ser Leu Thr Asn Asp Ser Ala Leu
            275                 280                 285

Asp Ile Ala Ala Tyr Gly Ser Gly Ile Lys His Val Ile Lys Glu Ser
        290                 295                 300

Trp Glu Gly Tyr Gly Met Asp Phe Tyr Ser Ile Gly Thr Tyr Asp Ala
305                 310                 315                 320

Phe Asn Asp Lys Trp Thr Pro Asp Asn Pro Glu Leu Asp Val Gly Ile
                325                 330                 335

Gly Leu Arg Cys Asp Tyr Gly Arg Phe Phe Ala Ser Lys Ser Ile Phe
            340                 345                 350

Asp Pro Val Lys Lys Arg Arg Ile Thr Trp Ala Tyr Val Gly Glu Ser
        355                 360                 365

Asp Asn Ala Asp Asp Asp Leu Ser Arg Gly Trp Ala Thr Ile Tyr Asn
370                 375                 380

Val Gly Arg Thr Ile Val Leu Asp Arg Lys Thr Gly Thr His Leu Leu
385                 390                 395                 400

His Trp Pro Val Glu Glu Ile Glu Ser Leu Arg Tyr Asn Gly Gln Glu
                405                 410                 415

Phe Lys Glu Ile Lys Leu Glu Pro Gly Ser Ile Ala Pro Leu Asp Ile
            420                 425                 430

Gly Thr Ala Thr Gln Leu Asp Ile Val Ala Thr Phe Lys Val Asp Glu
        435                 440                 445

Ala Ala Leu Asn Ala Thr Ser Glu Thr Asp Asp Asn Phe Ala Cys Thr
450                 455                 460

Thr Ser Ser Gly Ala Val Glu Arg Gly Ser Leu Gly Pro Phe Gly Leu
465                 470                 475                 480

Ala Val Leu Ala Asp Gly Thr Leu Ser Glu Leu Thr Pro Val Tyr Phe
                485                 490                 495

Tyr Ile Ala Lys Lys Ala Asp Gly Val Ser Thr His Phe Cys Thr
            500                 505                 510

Asp Lys Leu Arg Ser Ser Leu Asp Phe Asp Lys Glu Arg Val Val Tyr
        515                 520                 525

Gly Ser Thr Val Pro Val Leu Asp Asp Glu Glu Leu Thr Met Arg Leu
530                 535                 540

Leu Val Asp His Ser Val Val Glu Ala Phe Ala Gln Gly Gly Arg Ile
545                 550                 555                 560

Ala Ile Thr Ser Arg Val Tyr Pro Thr Lys Ala Ile Tyr Glu Gly Ala
                565                 570                 575

Lys Leu Phe Leu Phe Asn Asn Ala Thr Asp Thr Ser Val Lys Ala Ser
            580                 585                 590

Leu Lys Ile Trp Gln Met Ala Ser Ala Gln Ile His Gln Tyr Glu Phe
        595                 600                 605

Asn
```

<210> SEQ ID NO 5
<211> LENGTH: 1333
<212> TYPE: DNA
<213> ORGANISM: Helianthus sp.

<400> SEQUENCE: 5

```
gcacgaggtc aacagtctgg acaggtcccg atggaaagca taggatgatc atgggatcta      60
aacgtggcaa tacaggcatg atactcgttt accataccac cgattacacg aactacgagt     120
tgttggatga gccgttgcac tccgttccca acaccgatat gtgggaatgc gtcgactttt     180
acccggtttc gttaaccaat gatagtgcac ttgatatggc ggcctatggg tcgggtatca     240
aacacgttat taagaaagt tgggagggac atggaatgga ttggtattca atcgggacat     300
atgacgcgat aaatgataaa tggactcccg ataacccgga actagatgtc ggtatcgggt     360
tacggtgcga ttacgggaag ttttttgcat caaagagtct ttatgaccca ttgaagaaaa     420
ggagggtcac ttgggcttat gttggagaat cagatagtgt tgaccaggac ctctctagag     480
gatgggctac tgtttataat gttggaagaa caattgtact agatagaaaa accgggaccc     540
atttacttca ttggcccgtt gaggaggtcg agagtttgag atacaacggt caggagttta     600
aagagatcga gctagagccc ggttcaatca ttccactcga cataggcacg gctacacagt     660
tggacatagt tgcaacattt gaggtggatc aagcagcgtt gaacgcgaca agtgaaaccg     720
atgatattta tggttgcacc actagcttag gtgcagccca aaggggaagt ttgggaccat     780
ttggtcttgc ggttctagcc gatggaaccc tttctgagtt aactccggtt tatttctaca     840
ttgctaaaaa ggccgatgga ggtttgtcga cacattttg taccgataag ctaaggtcat     900
cactggatta tgatggacag agagtggtgt atgggagcac tgttcctgtg ttagatgatg     960
aagaactcac aatgaggcta ttggtggatc attcgatagt agaggggttt gcgcaaggag    1020
gaaggacggt tataacatca agggtgtatc caacaaaagc gatatacgaa caagcgaagt    1080
tgttcttgtt caacaacgct acaggtacga gtgtgaaggc atctctcaag atttggcaaa    1140
tggcttctgc acaaattcat caatactcgt tttaattacc ggctattgct atcttttgt    1200
tattggtatt tatgtatctt aatttctttt taaaccttt tatttgataa atattggttc     1260
ttgttattgt gattctagta gtaaatgaat ggtgttttgg gttatctgtt aaaaaaaaaa    1320
aaaaaaaaa aaa                                                        1333
```

<210> SEQ ID NO 6
<211> LENGTH: 390
<212> TYPE: PRT
<213> ORGANISM: Helianthus sp.

<400> SEQUENCE: 6

```
Thr Arg Ser Thr Val Trp Thr Gly Pro Asp Gly Lys His Arg Met Ile
 1               5                  10                  15

Met Gly Ser Lys Arg Gly Asn Thr Gly Met Ile Leu Val Tyr His Thr
            20                  25                  30

Thr Asp Tyr Thr Asn Tyr Glu Leu Leu Asp Glu Pro Leu His Ser Val
        35                  40                  45

Pro Asn Thr Asp Met Trp Glu Cys Val Asp Phe Tyr Pro Val Ser Leu
    50                  55                  60

Thr Asn Asp Ser Ala Leu Asp Met Ala Ala Tyr Gly Ser Gly Ile Lys
65                  70                  75                  80

His Val Ile Lys Glu Ser Trp Glu Gly His Gly Met Asp Trp Tyr Ser
                85                  90                  95
```

```
Ile Gly Thr Tyr Asp Ala Ile Asn Asp Lys Trp Thr Pro Asp Asn Pro
                100                 105                 110
Glu Leu Asp Val Gly Ile Gly Leu Arg Cys Asp Tyr Gly Lys Phe Phe
            115                 120                 125
Ala Ser Lys Ser Leu Tyr Asp Pro Leu Lys Lys Arg Arg Val Thr Trp
130                 135                 140
Ala Tyr Val Gly Glu Ser Asp Ser Val Asp Gln Asp Leu Ser Arg Gly
145                 150                 155                 160
Trp Ala Thr Val Tyr Asn Val Gly Arg Thr Ile Val Leu Asp Arg Lys
                165                 170                 175
Thr Gly Thr His Leu Leu His Trp Pro Val Glu Glu Val Glu Ser Leu
            180                 185                 190
Arg Tyr Asn Gly Gln Glu Phe Lys Glu Ile Glu Leu Glu Pro Gly Ser
        195                 200                 205
Ile Ile Pro Leu Asp Ile Gly Thr Ala Thr Gln Leu Asp Ile Val Ala
    210                 215                 220
Thr Phe Glu Val Asp Gln Ala Ala Leu Asn Ala Thr Ser Glu Thr Asp
225                 230                 235                 240
Asp Ile Tyr Gly Cys Thr Thr Ser Leu Gly Ala Gln Arg Gly Ser
                245                 250                 255
Leu Gly Pro Phe Gly Leu Ala Val Leu Ala Asp Gly Thr Leu Ser Glu
            260                 265                 270
Leu Thr Pro Val Tyr Phe Tyr Ile Ala Lys Lys Ala Asp Gly Gly Leu
        275                 280                 285
Ser Thr His Phe Cys Thr Asp Lys Leu Arg Ser Ser Leu Asp Tyr Asp
    290                 295                 300
Gly Gln Arg Val Val Tyr Gly Ser Thr Val Pro Val Leu Asp Asp Glu
305                 310                 315                 320
Glu Leu Thr Met Arg Leu Leu Val Asp His Ser Ile Val Glu Gly Phe
                325                 330                 335
Ala Gln Gly Gly Arg Thr Val Ile Thr Ser Arg Val Tyr Pro Thr Lys
            340                 345                 350
Ala Ile Tyr Glu Gln Ala Lys Leu Phe Leu Phe Asn Asn Ala Thr Gly
        355                 360                 365
Thr Ser Val Lys Ala Ser Leu Lys Ile Trp Gln Met Ala Ser Ala Gln
    370                 375                 380
Ile His Gln Tyr Ser Phe
385                 390

<210> SEQ ID NO 7
<211> LENGTH: 1844
<212> TYPE: DNA
<213> ORGANISM: Triticum aestivum

<400> SEQUENCE: 7
gcacgaggtg gggccacgcc gtctctcgga accttgtcac gtggcgcacc ctccctattg      60
ccatggtggc cgaccagtgg tacgacatcc tcgggtcct ctcgggctct atgacggtgc     120
tacccaatgg caccgtcatc atgatctaca cgggggccac caacgcctcc gccattgagg     180
tgcagtgcat cgccacccc gccgacccca cgacccctt cctccgccgc tggaccaagc      240
accccgcgaa ccccgtcatc tggtcgccgc ggggatcgg caccaaggat tttcgagacc     300
cgatgaccgc ttggtacgat gaatctgatg acacatggcg caccctcctc gggtccaagg     360
acgaccagga cggccaccac gatgggatcg ccatgatgta caagaccaag gacttcctta     420
actatgagct catcccgggc atcttgcatc gagtcgagcg caccggcgag tgggagtgca     480
```

```
tcgacttcta ccctgtcggt cgccgtagca gcgacaactc atcggagatg ttgcacgtgt    540
tgaaggcgag catggacgat gaacgacacg actactactc gctaggcacg tacgactcgg    600
cagcaaacac gttgacgccg attgacccgg acctcgactt ggggatcggg ctgaggtacg    660
attggggtaa gttttatgcg tccacctcgt tctatgatcc ggcgaagaag cggcgcgtgc    720
tgatggggta cgtcggcgag gtcgactcca agcgggctga tgtcgtgaag ggatgggcct    780
caattcagtc agttccaagg acaattgctc tcgacgagaa gacccggacg aacctcctcc    840
tctggcccgt ggaggagatt gagaccctcc gcctcaatgc cactgaactt agcgacgtca    900
ccatgaacac cggctccgtc atccatatcc ccctccgcca aggcactcag cttgacatcg    960
aggcaacttt ccaccttgat gcttctgccg tcgctgccct caatgaggcc gatgtgggct   1020
acaactgcag cagcagcggc ggtgctgtta accgcggcgc gctaggcccc ttcggcctcc   1080
tcgtcctcgc tgctggtgac cgccgcggcg agcaaacggc ggtgtacttc tacgtgtcta   1140
ggggccttga tggaggcctc ataccagct tctgccaaga tgagttacgg tcgtcacggg    1200
ccaaggacgt gacaaagcgg gtgattggga gcacggtgcc ggtgctcgac ggcgaggctt   1260
tctcaatgag ggtgctcgtg gaccactcca tcgtgcaggg cttcgcgatg gcgggagga   1320 ccacgatgac gtcgcgggtg tacccgatgg aggcctatca ggaggcaaaa gtgtacttgt   1380
tcaacaatgc caccggtgcc agcgttatgg cggaaaggct cgtcgtgcac gagatggact   1440
cggcacacaa ccagctctcc aatatggacg attactcgta tgttcaatga gctcttgca    1500 tctcatcagt aataagctac attggatcaa agacgctcac caaggaaggc caagacatat   1560
gtaaacgatt ccgcacagcc tcgcttgcag aattgaaaca tctatccttg ggtcatgttc   1620
tgcattgatg tcacagtgaa ctatattact ttgttgggtg taggatcgat atagtttggg   1680
tgggtggaac tttgtttgtt tacatagtga accggtgtgg tctgcgtaat aagcttacgt   1740
gtttgtttag aaaatgaact attgttgttc gggagaaaaa aaaaaaaaaa aaaaaaaaaa   1800 aaaaaaaaa aaaaaaaaa aaaaaaaaa aaaaaaaaa aaaa                       1844
```

<210> SEQ ID NO 8
<211> LENGTH: 495
<212> TYPE: PRT
<213> ORGANISM: Triticum aestivum

<400> SEQUENCE: 8

```
Thr Arg Trp Gly His Ala Val Ser Arg Asn Leu Val Thr Trp Arg Thr
  1               5                  10                  15

Leu Pro Ile Ala Met Val Ala Asp Gln Trp Tyr Asp Ile Leu Gly Val
             20                  25                  30

Leu Ser Gly Ser Met Thr Val Leu Pro Asn Gly Thr Val Ile Met Ile
         35                  40                  45

Tyr Thr Gly Ala Thr Asn Ala Ser Ala Ile Glu Val Gln Cys Ile Ala
     50                  55                  60

Thr Pro Ala Asp Pro Asn Asp Pro Phe Leu Arg Arg Trp Thr Lys His
 65                  70                  75                  80

Pro Ala Asn Pro Val Ile Trp Ser Pro Pro Gly Ile Gly Thr Lys Asp
                 85                  90                  95

Phe Arg Asp Pro Met Thr Ala Trp Tyr Asp Glu Ser Asp Asp Thr Trp
            100                 105                 110

Arg Thr Leu Leu Gly Ser Lys Asp Asp Gln Asp Gly His His Asp Gly
        115                 120                 125

Ile Ala Met Met Tyr Lys Thr Lys Asp Phe Leu Asn Tyr Glu Leu Ile
```

```
           130                 135                 140
Pro Gly Ile Leu His Arg Val Glu Arg Thr Gly Glu Trp Glu Cys Ile
145                 150                 155                 160

Asp Phe Tyr Pro Val Gly Arg Arg Ser Ser Asp Asn Ser Ser Glu Met
                165                 170                 175

Leu His Val Leu Lys Ala Ser Met Asp Asp Glu Arg His Asp Tyr Tyr
                180                 185                 190

Ser Leu Gly Thr Tyr Asp Ser Ala Ala Asn Thr Trp Thr Pro Ile Asp
                195                 200                 205

Pro Asp Leu Asp Leu Gly Ile Gly Leu Arg Tyr Asp Trp Gly Lys Phe
210                 215                 220

Tyr Ala Ser Thr Ser Phe Tyr Asp Pro Ala Lys Lys Arg Arg Val Leu
225                 230                 235                 240

Met Gly Tyr Val Gly Glu Val Asp Ser Lys Arg Ala Asp Val Val Lys
                245                 250                 255

Gly Trp Ala Ser Ile Gln Ser Val Pro Arg Thr Ile Ala Leu Asp Glu
                260                 265                 270

Lys Thr Arg Thr Asn Leu Leu Leu Trp Pro Val Glu Glu Ile Glu Thr
                275                 280                 285

Leu Arg Leu Asn Ala Thr Glu Leu Ser Asp Val Thr Met Asn Thr Gly
290                 295                 300

Ser Val Ile His Ile Pro Leu Arg Gln Gly Thr Gln Leu Asp Ile Glu
305                 310                 315                 320

Ala Thr Phe His Leu Asp Ala Ser Ala Val Ala Ala Leu Asn Glu Ala
                325                 330                 335

Asp Val Gly Tyr Asn Cys Ser Ser Ser Gly Gly Ala Val Asn Arg Gly
                340                 345                 350

Ala Leu Gly Pro Phe Gly Leu Leu Val Leu Ala Ala Gly Asp Arg Arg
                355                 360                 365

Gly Glu Gln Thr Ala Val Tyr Phe Tyr Val Ser Arg Gly Leu Asp Gly
370                 375                 380

Gly Leu His Thr Ser Phe Cys Gln Asp Glu Leu Arg Ser Ser Arg Ala
385                 390                 395                 400

Lys Asp Val Thr Lys Arg Val Ile Gly Ser Thr Val Pro Val Leu Asp
                405                 410                 415

Gly Glu Ala Phe Ser Met Arg Val Leu Val Asp His Ser Ile Val Gln
                420                 425                 430

Gly Phe Ala Met Gly Gly Arg Thr Thr Met Thr Ser Arg Val Tyr Pro
                435                 440                 445

Met Glu Ala Tyr Gln Glu Ala Lys Val Tyr Leu Phe Asn Asn Ala Thr
450                 455                 460

Gly Ala Ser Val Met Ala Glu Arg Leu Val Val His Glu Met Asp Ser
465                 470                 475                 480

Ala His Asn Gln Leu Ser Asn Met Asp Asp Tyr Ser Tyr Val Gln
                485                 490                 495

<210> SEQ ID NO 9
<211> LENGTH: 1612
<212> TYPE: DNA
<213> ORGANISM: Triticum aestivum

<400> SEQUENCE: 9
gcacgagacg acatcctggg ggtcctttcg ggctctatga cggtgctacc aaatggcacg      60
gtcatcatga tctacacggg ggccaccaac gcctctgccg ttgaggtgca gtgcatcgcc     120
```

```
acccccgccg accccaacga cccottcctc cgccgctgga ccaagcaccc cgccaaccc      180
gtcatctggt cgccgccggg gatcggcacc aaggattttc gagacccgat gactgcttgg    240
tacgatgaat ctgatgacac atggcgcacc ctccttgggt ccaaggatga ccacgacggt    300
caccacgatg ggatcgccat gatgtacaag accaaggact ccttaactac gagctcatc    360
ccgggtatct tgcatcgagt ccagcgcacc ggcgagtggg agtgcattga cttctaccct   420
gtcggccaca gaagcaacga caactcatcg agatgttgc acgtgttgaa ggcgagcatg    480
gacgacgaac ggcacgacta ctactcgcta ggcacgtacg actcggcagc aaacgcgtgg    540
acgccgatcg acccggagct cgacttgggg atcgggctga gatacgactg gggtaagttt    600
tatgcgtcca cctcgttcta tgatccggca agaagcggc gcgtgctgat ggggtacgtc     660
ggcgaggtcg actccaagcg ggctgatgtc gtgaagggat gggcctcgat tcagtcagtt    720
ccaaggacaa ttgctctcga cgagaagacc cggacgaacc tcctcctctg gcccgtggag    780
gagattgaga ccctccgcct caacgccacc gaacttagcg acgtcaccct taacaccggc    840
tccgtcatcc atatcccgct ccgccaaggc actcagctcg acatcgaggc aactttccac    900
cttgatgctt ctgccgtcgc tgccctcaat gaggccgatg tgggctacaa ctgcagcagc    960
agcggcggtg ctgttaaccg cggcgcgcta ggccccttcg gcctcctcgt cctcgctgct   1020
ggtgaccgcc gtggcgagca acgcgcggtg tatttctacg tgtctagggg gctcgacgga   1080
ggcctccata ccagcttctg ccaagacgag ttgcggtcgt cacgggccaa ggatgtgacg   1140
aagcgggtga ttgggagcac ggtgccggtg ctcgacggcg aggctttctc gatgagggtg   1200
ctcgtggacc actccatcgt gcagggcttc gcgatgggcg ggaggaccac gatgacgtcg   1260
cgggtgtacc cgatggaggc ctatcaggag gcaaaagtgt acttgttcaa caatgcgacc   1320
ggtgccagcg tcatggcgga aaggctcgtc gtgcacgaga tggactcagc acacaaccag   1380
ctctccaata tggacgatca ctcgtatgtt caatgaagct cttgcatctc atcagtaata   1440
agctacattg gatcaaagac gcgcaccaag gaaggccaag acatatgtaa atgattccgc   1500
acagcctcgc ttgcagaatt gaaacatcta tccttgggtc atgttctgca ttgatgtcac   1560
tgtgaactac agtatattac tttgttgggc gtagaaaaaa aaaaaaaaaa aa           1612
```

<210> SEQ ID NO 10
<211> LENGTH: 471
<212> TYPE: PRT
<213> ORGANISM: Triticum aestivum

<400> SEQUENCE: 10

```
Ala Arg Asp Asp Ile Leu Gly Val Leu Ser Gly Ser Met Thr Val Leu
 1               5                  10                  15

Pro Asn Gly Thr Val Ile Met Ile Tyr Thr Gly Ala Thr Asn Ala Ser
                20                  25                  30

Ala Val Glu Val Gln Cys Ile Ala Thr Pro Ala Asp Pro Asn Asp Pro
            35                  40                  45

Phe Leu Arg Arg Trp Thr Lys His Pro Ala Asn Pro Val Ile Trp Ser
        50                  55                  60

Pro Pro Gly Ile Gly Thr Lys Asp Phe Arg Asp Pro Met Thr Ala Trp
 65                  70                  75                  80

Tyr Asp Glu Ser Asp Asp Thr Trp Arg Thr Leu Leu Gly Ser Lys Asp
                85                  90                  95

Asp His Asp Gly His His Asp Gly Ile Ala Met Met Tyr Lys Thr Lys
                100                 105                 110

Asp Phe Leu Asn Tyr Glu Leu Ile Pro Gly Ile Leu His Arg Val Gln
```

```
            115                 120                 125
Arg Thr Gly Glu Trp Glu Cys Ile Asp Phe Tyr Pro Val Gly His Arg
130                 135                 140

Ser Asn Asp Asn Ser Ser Glu Met Leu His Val Leu Lys Ala Ser Met
145                 150                 155                 160

Asp Asp Glu Arg His Asp Tyr Tyr Ser Leu Gly Thr Tyr Asp Ser Ala
                165                 170                 175

Ala Asn Ala Trp Thr Pro Ile Asp Pro Glu Leu Asp Leu Gly Ile Gly
                180                 185                 190

Leu Arg Tyr Asp Trp Gly Lys Phe Tyr Ala Ser Thr Ser Phe Tyr Asp
                195                 200                 205

Pro Ala Lys Lys Arg Arg Val Leu Met Gly Tyr Val Gly Glu Val Asp
    210                 215                 220

Ser Lys Arg Ala Asp Val Val Lys Gly Trp Ala Ser Ile Gln Ser Val
225                 230                 235                 240

Pro Arg Thr Ile Ala Leu Asp Glu Lys Thr Arg Thr Asn Leu Leu Leu
                245                 250                 255

Trp Pro Val Glu Glu Ile Glu Thr Leu Arg Leu Asn Ala Thr Glu Leu
                260                 265                 270

Ser Asp Val Thr Leu Asn Thr Gly Ser Val Ile His Ile Pro Leu Arg
                275                 280                 285

Gln Gly Thr Gln Leu Asp Ile Glu Ala Thr Phe His Leu Asp Ala Ser
290                 295                 300

Ala Val Ala Ala Leu Asn Glu Ala Asp Val Gly Tyr Asn Cys Ser Ser
305                 310                 315                 320

Ser Gly Gly Ala Val Asn Arg Gly Ala Leu Gly Pro Phe Gly Leu Leu
                325                 330                 335

Val Leu Ala Ala Gly Asp Arg Arg Gly Glu Gln Thr Ala Val Tyr Phe
                340                 345                 350

Tyr Val Ser Arg Gly Leu Asp Gly Gly Leu His Thr Ser Phe Cys Gln
                355                 360                 365

Asp Glu Leu Arg Ser Ser Arg Ala Lys Asp Val Thr Lys Arg Val Ile
370                 375                 380

Gly Ser Thr Val Pro Val Leu Asp Gly Glu Ala Phe Ser Met Arg Val
385                 390                 395                 400

Leu Val Asp His Ser Ile Val Gln Gly Phe Ala Met Gly Gly Arg Thr
                405                 410                 415

Thr Met Thr Ser Arg Val Tyr Pro Met Glu Ala Tyr Gln Glu Ala Lys
                420                 425                 430

Val Tyr Leu Phe Asn Asn Ala Thr Gly Ala Ser Val Met Ala Glu Arg
                435                 440                 445

Leu Val Val His Glu Met Asp Ser Ala His Asn Gln Leu Ser Asn Met
    450                 455                 460

Asp Asp His Ser Tyr Val Gln
465                 470

<210> SEQ ID NO 11
<211> LENGTH: 476
<212> TYPE: DNA
<213> ORGANISM: Triticum aestivum

<400> SEQUENCE: 11
gcacgagcca cgatgacgtc gcgggtgtac ccgatggagg cctatcagga ggcaaaagtg      60
tacttgttca acaatgccac cggtgccagc gttacggcgg aaaggctcgt cgtgcacgag     120
```

```
atggactcag cacacaacca gctctccaat atggacgatt actcgtatgt tcaatgaagc    180
tcttgcatct catcagtaat aagctacatt ggatcaaaga cgctcaccaa ggaaggccaa    240
gacatatatt taaacgattc cgcacagcct cgcttgcaga attgaaacat ctatccttgg    300
gtcatgttct gcattgatgt cacagtgaac tatattactt tgttgggtgt aggatcgata    360
tagtttgggt gggtggaact ttgtttgttt acatagtgaa ccggtgtggt ctgcataata    420
agcttatgtg tttgtttaga aaatgaatta ttgttgttaa aaaaaaaaaa aaaaaa        476

<210> SEQ ID NO 12
<211> LENGTH: 58
<212> TYPE: PRT
<213> ORGANISM: Triticum aestivum

<400> SEQUENCE: 12

Ala Arg Ala Thr Met Thr Ser Arg Val Tyr Pro Met Glu Ala Tyr Gln
  1               5                  10                  15

Glu Ala Lys Val Tyr Leu Phe Asn Asn Ala Thr Gly Ala Ser Val Thr
             20                  25                  30

Ala Glu Arg Leu Val Val His Glu Met Asp Ser Ala His Asn Gln Leu
         35                  40                  45

Ser Asn Met Asp Asp Tyr Ser Tyr Val Gln
     50                  55

<210> SEQ ID NO 13
<211> LENGTH: 2093
<212> TYPE: DNA
<213> ORGANISM: Parthenium argentatum Grey

<400> SEQUENCE: 13
gcacgagcgt gtacatagta aaaaaaccct ccagccacca catgatggct tcatctacca     60
ccacctcccc tctcattctc cacgatgatc ctgaaaacct ccaggaaccc accggattta    120
cgggggttcg tcgtccatcc atcgcaaaag cgctttgcgt aacccttgtt tcggttatgg    180
taatctgtgg tctggttgct gtaatcagca accagacaca ggtaccacaa gtagccaaca    240
gccatcaagg tgccgccacc acattcacaa ctcagttgcc aaaaatagat atgaaacggg    300
ttccgggaga gttggattcg ggtgctgatg tccaatggca acgctccgct tatcattttc    360
aacctgacaa aaactacatt agtgatcctg atggcccaat gtatcacatg ggatggtacc    420
atctatttta tcagtacaac ccagaatctg ccatatgggg caacatcaca tgggtcact    480 ccgtatccaa agacatgatc aactggttcc atctccctt cgccatggtt ccggaccatt    540
ggtacgacat cgaaggcgtc atgacaggtt ccgccacagt cctcccaaac ggtgagatca    600
tcatgcttta cacgggcaat gcgtacgatc tctcccaagt acaatgctta gcgtacgcag    660
tcaactcatc agatccactt cttatagagt ggaaaaaata cgaaggcaac ccggttttat    720
tgccgccgcc aggggtgggt tacaaggatt tcgggacccc atctacattg tggctgggcc    780
ccgatggtga atatagaatg gtaatggggt ccaagcacaa cgagactatt ggttgtgctt    840
tgatttacca taccactaat tttacgcatt ttgaattgaa tgaggaggtg cttcatgcgg    900
tcccacatac tggtatgtgg aatgcgttg atctttatcc ggtatccacc acacacacaa    960
acgggttgga catggtggat aatgggccaa atgtaaaata cgtgttgaaa caaagtgggg   1020
atgaagatcg ccatgattgg tatgcgattg aagttatga ttgggtgaat gataagtggt   1080
acccggatga cccggaaaac gatgtgggta tcgggttaag atacgattac ggaaagtttt   1140
atgcgtccaa gacgttttat gaccaacata agaaaaggag ggtcctttgg ggctatgttg   1200
```

```
gagaaaccga tcccgaaaag tatgacctta caaagggatg ggctaacata ttgaatattc    1260
caaggaccgt cgttttggac acgaaaacta aaaccaattt gattcaatgg ccaattgagg    1320
aaaccgaaaa acttaggtcg aaaaagtatg ataaatttgt agatgtggag cttcgacccg    1380
ggtcactcat tcccctcgag ataggtacag ccacacagtt ggatatagtt gcgacattcg    1440
aagttgatca aatgatgttg gaatcaacgc tagaagccga tgttctattc aactgcacga    1500
ctagtgttgg ctcagttgga aggggcgtgt gggaccgtt tggtgtggtg gttctagctg     1560
atgcccagcg caccgaacaa cttcctgtgt atttctatat tgcaaaagat accgacggga    1620
cgtcaagaac ctacttttgt gctgatgaaa caagatcatc caaggatgta acgtggggaa    1680
aatgggtgta tggaagcagt gttcctgtcc tccctaacga aaagtacaat atgaggttac    1740
tggtggatca ttcgatagtg gagggatttg cacaaaacgg aagaacggtg gtgacatcga    1800
gagtgtatcc aacgaaggca atttacaacg ctgcgaaggt gttttttgttc aacaacgcga    1860 ccgggattag ggtgaaggcg tcggtcaaga tttggaagat ggcggaagca gaactcaacc    1920
ctttcccagt tactgggtgg acttcttgat ggctagattt tggtccctat atgtgtgtgt    1980
tactatcgtg aggtatatgt cttggactgt gggggtatta ttgtaatttg atatgtatgt    2040
tctgttactt ttgaggttct agtttaaaaa aaaaaaaaaa aaaaaaaaa aaa            2093
```

<210> SEQ ID NO 14
<211> LENGTH: 635
<212> TYPE: PRT
<213> ORGANISM: Parthenium argentatum Grey

<400> SEQUENCE: 14

```
Met Met Ala Ser Ser Thr Thr Thr Ser Pro Leu Ile Leu His Asp Asp
 1               5                  10                  15

Pro Glu Asn Leu Gln Glu Pro Thr Gly Phe Thr Gly Val Arg Arg Pro
                20                  25                  30

Ser Ile Ala Lys Ala Leu Cys Val Thr Leu Val Ser Val Met Val Ile
            35                  40                  45

Cys Gly Leu Val Ala Val Ile Ser Asn Gln Thr Gln Val Pro Gln Val
        50                  55                  60

Ala Asn Ser His Gln Gly Ala Ala Thr Thr Phe Thr Thr Gln Leu Pro
 65                 70                  75                  80

Lys Ile Asp Met Lys Arg Val Pro Gly Glu Leu Asp Ser Gly Ala Asp
                85                  90                  95

Val Gln Trp Gln Arg Ser Ala Tyr His Phe Gln Pro Asp Lys Asn Tyr
           100                 105                 110

Ile Ser Asp Pro Asp Gly Pro Met Tyr His Met Gly Trp Tyr His Leu
        115                 120                 125

Phe Tyr Gln Tyr Asn Pro Glu Ser Ala Ile Trp Gly Asn Ile Thr Trp
   130                  135                 140

Gly His Ser Val Ser Lys Asp Met Ile Asn Trp Phe His Leu Pro Phe
145                 150                 155                 160

Ala Met Val Pro Asp His Trp Tyr Asp Ile Glu Gly Val Met Thr Gly
                165                 170                 175

Ser Ala Thr Val Leu Pro Asn Gly Glu Ile Ile Met Leu Tyr Thr Gly
            180                 185                 190

Asn Ala Tyr Asp Leu Ser Gln Val Gln Cys Leu Ala Tyr Ala Val Asn
        195                 200                 205

Ser Ser Asp Pro Leu Leu Ile Glu Trp Lys Lys Tyr Glu Gly Asn Pro
    210                 215                 220
```

```
Val Leu Leu Pro Pro Gly Val Gly Tyr Lys Asp Phe Arg Asp Pro
225                 230                 235                 240

Ser Thr Leu Trp Leu Gly Pro Asp Gly Glu Tyr Arg Met Val Met Gly
            245                 250                 255

Ser Lys His Asn Glu Thr Ile Gly Cys Ala Leu Ile Tyr His Thr Thr
        260                 265                 270

Asn Phe Thr His Phe Glu Leu Asn Glu Glu Val Leu His Ala Val Pro
    275                 280                 285

His Thr Gly Met Trp Glu Cys Val Asp Leu Tyr Pro Val Ser Thr Thr
290                 295                 300

His Thr Asn Gly Leu Asp Met Val Asp Asn Gly Pro Asn Val Lys Tyr
305                 310                 315                 320

Val Leu Lys Gln Ser Gly Asp Glu Asp Arg His Asp Trp Tyr Ala Ile
            325                 330                 335

Gly Ser Tyr Asp Trp Val Asn Asp Lys Trp Tyr Pro Asp Asp Pro Glu
        340                 345                 350

Asn Asp Val Gly Ile Gly Leu Arg Tyr Asp Tyr Gly Lys Phe Tyr Ala
    355                 360                 365

Ser Lys Thr Phe Tyr Asp Gln His Lys Lys Arg Arg Val Leu Trp Gly
370                 375                 380

Tyr Val Gly Glu Thr Asp Pro Glu Lys Tyr Asp Leu Thr Lys Gly Trp
385                 390                 395                 400

Ala Asn Ile Leu Asn Ile Pro Arg Thr Val Leu Asp Thr Lys Thr
            405                 410                 415

Lys Thr Asn Leu Ile Gln Trp Pro Ile Glu Glu Thr Glu Lys Leu Arg
        420                 425                 430

Ser Lys Lys Tyr Asp Lys Phe Val Asp Val Glu Leu Arg Pro Gly Ser
    435                 440                 445

Leu Ile Pro Leu Glu Ile Gly Thr Ala Thr Gln Leu Asp Ile Val Ala
450                 455                 460

Thr Phe Glu Val Asp Gln Met Met Leu Glu Ser Thr Leu Glu Ala Asp
465                 470                 475                 480

Val Leu Phe Asn Cys Thr Thr Ser Val Gly Ser Val Gly Arg Gly Val
            485                 490                 495

Leu Gly Pro Phe Gly Val Val Leu Ala Asp Ala Gln Arg Thr Glu
        500                 505                 510

Gln Leu Pro Val Tyr Phe Tyr Ile Ala Lys Asp Thr Asp Gly Thr Ser
    515                 520                 525

Arg Thr Tyr Phe Cys Ala Asp Glu Thr Arg Ser Ser Lys Asp Val Asp
530                 535                 540

Val Gly Lys Trp Val Tyr Gly Ser Ser Val Pro Val Leu Pro Asn Glu
545                 550                 555                 560

Lys Tyr Asn Met Arg Leu Leu Val Asp His Ser Ile Val Glu Gly Phe
            565                 570                 575

Ala Gln Asn Gly Arg Thr Val Val Thr Ser Arg Val Tyr Pro Thr Lys
        580                 585                 590

Ala Ile Tyr Asn Ala Ala Lys Val Phe Leu Phe Asn Asn Ala Thr Gly
    595                 600                 605

Ile Arg Val Lys Ala Ser Val Lys Ile Trp Lys Met Ala Glu Ala Glu
610                 615                 620

Leu Asn Pro Phe Pro Val Thr Gly Trp Thr Ser
625                 630                 635

<210> SEQ ID NO 15
```

<211> LENGTH: 2107
<212> TYPE: DNA
<213> ORGANISM: Helianthus sp.

<400> SEQUENCE: 15

| | | | | | |
|---|---|---|---|---|---|
| gcaccacaac | acacttaagt | gcgtgtacat | aataaagaaa | aaaccctcct gccaccacat | 60 |
| gatggcttca | tccaccacca | ccacccctct | cattctccat | gatgaccctg aaaacctccc | 120 |
| agaactcacc | ggatctccga | caactcgtcg | tctatccatc | gcaaaagtgc tttcggggat | 180 |
| ccttgtttcg | gttctagtta | catgtgctct | tgttgcttta | atcaacaacc aaacatatga | 240 |
| accacccgcg | gccaccacat | tcgcaactca | gttgccaaat | attgatctga agcgggttcc | 300 |
| aggaaagttg | gattcgagtg | ctgaggttga | atggcaacga | tccgcttatc attttcaacc | 360 |
| cgacaaaaat | ttcattagtg | atcctgatgg | cccaatgtat | cacatgggat ggtaccatct | 420 |
| attctatcag | tacaaccctg | aatctgccat | ctggggcaac | atcacatggg gccactcggt | 480 |
| atcgaaagac | atgatcaact | ggttccatct | ccctttcgcc | atggttcctg accattggta | 540 |
| cgacatcgaa | ggtgtcatga | cgggttcggc | tacagtcctc | cctaatggtc aaatcatcat | 600 |
| gctttacacg | gcaacgcgt | acgatctctc | ccaagtacaa | tgcttggcat acgctgtcaa | 660 |
| ctcgtcggat | ccccttctta | tagagtggaa | aaaatatgaa | ggtaaccctg tcttgttccc | 720 |
| accaccagga | gtgggctaca | aggactttcg | ggacccatcc | acattgtggt tgggccctga | 780 |
| tggtgaatat | agaatggtaa | tggggtccaa | gcacaacgag | actattggat gtgctttgat | 840 |
| ttaccatacc | actaatttta | cgcatttga | attgaaagag | gaggtgcttc atgcagtccc | 900 |
| acatactggt | atgtgggaat | gtgttgatct | tacccagtg | tccaccgtac acacaaacgg | 960 |
| gttggacatg | gtggataacg | ggccaaatgt | taaatacgtg | ttgaaacaaa gtggggatga | 1020 |
| agatcgccat | gattggtatg | caattggaag | ttatgatgtg | gtgaatgata agtggtaccc | 1080 |
| ggatgacccg | gaaaatgatg | tgggtattgg | attaagatat | gatttttggaa aattttatgc | 1140 |
| gtccaagact | ttttatgacc | aacataagaa | gaggagggtc | ctttggggct atgttggaga | 1200 |
| aaccgatccc | caaagtatg | acatttcaaa | gggatgggct | aacatttga atattccaag | 1260 |
| aaccgtcgtt | ttggacacaa | aaaccaaaac | caatttgatt | caatggccaa tcgaggaaac | 1320 |
| cgaaaacctt | aggtcaaaaa | cgtacgatga | atttaaagac | gtggagcttc gacccgggtc | 1380 |
| actcgttccc | cttgagatag | gcacagccac | acagttggat | atagttgcga cattcgaaat | 1440 |
| cgaccaaaag | atgttggaat | caacgctaga | ggccgatgtt | ctattcaatt gcacgactag | 1500 |
| tgaaggctcg | gttgcaaggg | gtgcgttggg | accgttggt | gtggtggttc tagccgatgc | 1560 |
| ccaacgctcc | gaacaacttc | ctgtatactt | ctatatcgca | aaagatatcg atggaacctc | 1620 |
| acgaacttac | ttttgtgccg | atgaaacaag | atcatccaag | gatgtaagcg tagggaaatg | 1680 |
| ggtgtacgga | agcagtgttc | ctgtcctccc | aggcgaaaag | tacaatatga ggttattggt | 1740 |
| ggatcattcg | atagtggagg | gatttgcaca | aaacgggaga | accgtggtga catcaagagt | 1800 |
| gtatccaaca | aaggcgatct | acaacgctgc | gaaggtgttt | tgttcaaca acgcgactgg | 1860 |
| gatcagtgtg | aaggcgtcga | tcaagatctg | gaagatggcg | aaagcagaac tcaatccttt | 1920 |
| ccctcttcct | gggtggactt | tgaactttg | atggttagat | tttggaccct atatagttat | 1980 |
| tatcatgaag | cataagtttg | gactggaggg | ggtattattg | taattttata tgcatgttct | 2040 |
| attacttgtg | agtttatagt | atataattaa | attattatta | ttaaaaaaaa aaaaaaaaaa | 2100 |
| aaaaaaa | | | | | 2107 |

<210> SEQ ID NO 16

<211> LENGTH: 630
<212> TYPE: PRT
<213> ORGANISM: Helianthus sp.

<400> SEQUENCE: 16

```
Met Met Ala Ser Ser Thr Thr Thr Thr Pro Leu Ile Leu His Asp Asp
  1               5                  10                  15

Pro Glu Asn Leu Pro Glu Leu Thr Gly Ser Pro Thr Thr Arg Arg Leu
             20                  25                  30

Ser Ile Ala Lys Val Leu Ser Gly Ile Leu Val Ser Val Leu Val Thr
         35                  40                  45

Cys Ala Leu Val Ala Leu Ile Asn Asn Gln Thr Tyr Glu Pro Pro Ala
 50                  55                  60

Ala Thr Thr Phe Ala Thr Gln Leu Pro Asn Ile Asp Leu Lys Arg Val
 65                  70                  75                  80

Pro Gly Lys Leu Asp Ser Ser Ala Glu Val Glu Trp Gln Arg Ser Ala
                 85                  90                  95

Tyr His Phe Gln Pro Asp Lys Asn Phe Ile Ser Asp Pro Asp Gly Pro
            100                 105                 110

Met Tyr His Met Gly Trp Tyr His Leu Phe Tyr Gln Tyr Asn Pro Glu
            115                 120                 125

Ser Ala Ile Trp Gly Asn Ile Thr Trp Gly His Ser Val Ser Lys Asp
            130                 135                 140

Met Ile Asn Trp Phe His Leu Pro Phe Ala Met Val Pro Asp His Trp
145                 150                 155                 160

Tyr Asp Ile Glu Gly Val Met Thr Gly Ser Ala Thr Val Leu Pro Asn
                165                 170                 175

Gly Gln Ile Ile Met Leu Tyr Thr Gly Asn Ala Tyr Asp Leu Ser Gln
            180                 185                 190

Val Gln Cys Leu Ala Tyr Ala Val Asn Ser Ser Asp Pro Leu Leu Ile
            195                 200                 205

Glu Trp Lys Lys Tyr Glu Gly Asn Pro Val Leu Phe Pro Pro Pro Gly
            210                 215                 220

Val Gly Tyr Lys Asp Phe Arg Asp Pro Ser Thr Leu Trp Leu Gly Pro
225                 230                 235                 240

Asp Gly Glu Tyr Arg Met Val Met Gly Ser Lys His Asn Glu Thr Ile
                245                 250                 255

Gly Cys Ala Leu Ile Tyr His Thr Thr Asn Phe Thr His Phe Glu Leu
            260                 265                 270

Lys Glu Glu Val Leu His Ala Val Pro His Thr Gly Met Trp Glu Cys
            275                 280                 285

Val Asp Leu Tyr Pro Val Ser Thr Val His Thr Asn Gly Leu Asp Met
            290                 295                 300

Val Asp Asn Gly Pro Asn Val Lys Tyr Val Leu Lys Gln Ser Gly Asp
305                 310                 315                 320

Glu Asp Arg His Asp Trp Tyr Ala Ile Gly Ser Tyr Asp Val Val Asn
                325                 330                 335

Asp Lys Trp Tyr Pro Asp Pro Glu Asn Asp Val Gly Ile Gly Leu
            340                 345                 350

Arg Tyr Asp Phe Gly Lys Phe Tyr Ala Ser Lys Thr Phe Tyr Asp Gln
            355                 360                 365

His Lys Lys Arg Arg Val Leu Trp Gly Tyr Val Gly Glu Thr Asp Pro
            370                 375                 380

Gln Lys Tyr Asp Ile Ser Lys Gly Trp Ala Asn Ile Leu Asn Ile Pro
385                 390                 395                 400
```

```
Arg Thr Val Val Leu Asp Thr Lys Thr Lys Thr Asn Leu Ile Gln Trp
                405                 410                 415

Pro Ile Glu Glu Thr Glu Asn Leu Arg Ser Lys Thr Tyr Asp Glu Phe
            420                 425                 430

Lys Asp Val Glu Leu Arg Pro Gly Ser Leu Val Pro Leu Glu Ile Gly
            435                 440                 445

Thr Ala Thr Gln Leu Asp Ile Val Ala Thr Phe Glu Ile Asp Gln Lys
        450                 455                 460

Met Leu Glu Ser Thr Leu Glu Ala Asp Val Leu Phe Asn Cys Thr Thr
465                 470                 475                 480

Ser Glu Gly Ser Val Ala Arg Gly Ala Leu Gly Pro Phe Gly Val Val
                485                 490                 495

Val Leu Ala Asp Ala Gln Arg Ser Glu Gln Leu Pro Val Tyr Phe Tyr
            500                 505                 510

Ile Ala Lys Asp Ile Asp Gly Thr Ser Arg Thr Tyr Phe Cys Ala Asp
            515                 520                 525

Glu Thr Arg Ser Ser Lys Asp Val Ser Val Gly Lys Trp Val Tyr Gly
        530                 535                 540

Ser Ser Val Pro Val Leu Pro Gly Glu Lys Tyr Asn Met Arg Leu Leu
545                 550                 555                 560

Val Asp His Ser Ile Val Glu Gly Phe Ala Gln Asn Gly Arg Thr Val
                565                 570                 575

Val Thr Ser Arg Val Tyr Pro Thr Lys Ala Ile Tyr Asn Ala Ala Lys
            580                 585                 590

Val Phe Leu Phe Asn Asn Ala Thr Gly Ile Ser Val Lys Ala Ser Ile
            595                 600                 605

Lys Ile Trp Lys Met Ala Lys Ala Glu Leu Asn Pro Phe Pro Leu Pro
        610                 615                 620

Gly Trp Thr Phe Glu Leu
625                 630

<210> SEQ ID NO 17
<211> LENGTH: 615
<212> TYPE: PRT
<213> ORGANISM: Helianthus tuberosus

<400> SEQUENCE: 17

Met Gln Thr Pro Glu Pro Phe Thr Asp Leu Glu His Glu Pro His Thr
  1               5                  10                  15

Pro Leu Leu Asp His His His Asn Pro Pro Gln Thr Thr Thr Lys
                20                  25                  30

Pro Leu Phe Thr Arg Val Val Ser Gly Val Thr Phe Val Leu Phe Phe
            35                  40                  45

Phe Gly Phe Ala Ile Val Phe Ile Val Leu Asn Gln Gln Asn Ser Ser
        50                  55                  60

Val Arg Ile Val Thr Asn Ser Glu Lys Ser Phe Ile Arg Tyr Ser Gln
 65                  70                  75                  80

Thr Asp Arg Leu Ser Trp Glu Arg Thr Ala Phe His Phe Gln Pro Ala
                85                  90                  95

Lys Asn Phe Ile Tyr Asp Pro Asp Gly Gln Leu Phe His Met Gly Trp
            100                 105                 110

Tyr His Met Phe Tyr Gln Tyr Asn Pro Tyr Ala Pro Val Trp Gly Asn
        115                 120                 125

Met Ser Trp Gly His Ser Val Ser Lys Asp Met Ile Asn Trp Tyr Glu
    130                 135                 140
```

-continued

```
Leu Pro Val Ala Met Val Pro Thr Glu Trp Tyr Asp Ile Glu Gly Val
145                 150                 155                 160

Leu Ser Gly Ser Thr Thr Val Leu Pro Asn Gly Gln Ile Phe Ala Leu
                165                 170                 175

Tyr Thr Gly Asn Ala Asn Asp Phe Ser Gln Leu Gln Cys Lys Ala Val
            180                 185                 190

Pro Val Asn Leu Ser Asp Pro Leu Leu Ile Glu Trp Val Lys Tyr Glu
        195                 200                 205

Asp Asn Pro Ile Leu Tyr Thr Pro Gly Ile Gly Leu Lys Asp Tyr
210                 215                 220

Arg Asp Pro Ser Thr Val Trp Thr Gly Pro Asp Gly Lys His Arg Met
225                 230                 235                 240

Ile Met Gly Thr Lys Arg Gly Asn Thr Gly Met Val Leu Val Tyr Tyr
                245                 250                 255

Thr Thr Asp Tyr Thr Asn Tyr Glu Leu Leu Asp Glu Pro Leu His Ser
            260                 265                 270

Val Pro Asn Thr Asp Met Trp Glu Cys Val Asp Phe Tyr Pro Val Ser
        275                 280                 285

Leu Thr Asn Asp Ser Ala Leu Asp Met Ala Ala Tyr Gly Ser Gly Ile
290                 295                 300

Lys His Val Ile Lys Glu Ser Trp Glu His Gly Met Asp Trp Tyr
305                 310                 315                 320

Ser Ile Gly Thr Tyr Asp Ala Ile Asn Asp Lys Trp Thr Pro Asp Asn
                325                 330                 335

Pro Glu Leu Asp Val Gly Ile Gly Leu Arg Cys Asp Tyr Gly Arg Phe
            340                 345                 350

Phe Ala Ser Lys Ser Leu Tyr Asp Pro Leu Lys Lys Arg Arg Ile Thr
        355                 360                 365

Trp Gly Tyr Val Gly Glu Ser Asp Ser Ala Asp Gln Asp Leu Ser Arg
370                 375                 380

Gly Trp Ala Thr Val Tyr Asn Val Gly Arg Thr Ile Val Leu Asp Arg
385                 390                 395                 400

Lys Thr Gly Thr His Leu Leu His Trp Pro Val Glu Glu Val Glu Ser
                405                 410                 415

Leu Arg Tyr Asn Gly Gln Glu Phe Lys Glu Ile Lys Leu Glu Pro Gly
            420                 425                 430

Ser Ile Ile Pro Leu Asp Ile Gly Thr Ala Thr Gln Leu Asp Ile Val
        435                 440                 445

Ala Thr Phe Glu Val Asp Gln Ala Ala Leu Asn Ala Thr Ser Glu Thr
450                 455                 460

Asp Asp Ile Tyr Gly Cys Thr Thr Ser Leu Gly Ala Ala Gln Arg Gly
465                 470                 475                 480

Ser Leu Gly Pro Phe Gly Leu Ala Val Leu Ala Asp Gly Thr Leu Ser
                485                 490                 495

Glu Leu Thr Pro Val Tyr Phe Tyr Ile Ala Lys Lys Ala Asp Gly Gly
            500                 505                 510

Val Ser Thr His Phe Cys Thr Asp Lys Leu Arg Ser Ser Leu Asp Tyr
        515                 520                 525

Asp Gly Glu Arg Val Val Tyr Gly Gly Thr Val Pro Val Leu Asp Asp
530                 535                 540

Glu Glu Leu Thr Met Arg Leu Leu Val Asp His Ser Ile Val Glu Gly
545                 550                 555                 560

Phe Ala Gln Gly Gly Arg Thr Val Ile Thr Ser Arg Ala Tyr Pro Thr
```

```
                        565                 570                 575
Lys Ala Ile Tyr Glu Gln Ala Lys Leu Phe Leu Phe Asn Asn Ala Thr
                580                 585                 590

Gly Thr Ser Val Lys Ala Ser Leu Lys Ile Trp Gln Met Ala Ser Ala
                595                 600                 605

Pro Ile His Gln Tyr Pro Phe
            610                 615

<210> SEQ ID NO 18
<211> LENGTH: 630
<212> TYPE: PRT
<213> ORGANISM: Helianthus tuberosus

<400> SEQUENCE: 18

Met Met Ala Ser Ser Thr Thr Thr Thr Pro Leu Ile Leu His Asp Asp
  1               5                  10                  15

Pro Glu Asn Leu Pro Glu Leu Thr Gly Ser Pro Thr Thr Arg Arg Leu
             20                  25                  30

Ser Ile Ala Lys Val Leu Ser Gly Ile Leu Val Ser Val Leu Val Ile
         35                  40                  45

Gly Ala Leu Val Ala Leu Ile Asn Asn Gln Thr Tyr Glu Ser Pro Ser
     50                  55                  60

Ala Thr Thr Phe Val Thr Gln Leu Pro Asn Ile Asp Leu Lys Arg Val
 65                  70                  75                  80

Pro Gly Lys Leu Asp Ser Ser Ala Glu Val Glu Trp Gln Arg Ser Thr
                 85                  90                  95

Tyr His Phe Gln Pro Asp Lys Asn Phe Ile Ser Asp Pro Asp Gly Pro
            100                 105                 110

Met Tyr His Met Gly Trp Tyr His Leu Phe Tyr Gln Tyr Asn Pro Gln
        115                 120                 125

Ser Ala Ile Trp Gly Asn Ile Thr Trp Gly His Ser Val Ser Lys Asp
    130                 135                 140

Met Ile Asn Trp Phe His Leu Pro Phe Ala Met Val Pro Asp His Trp
145                 150                 155                 160

Tyr Asp Ile Glu Gly Val Met Thr Gly Ser Ala Thr Val Leu Pro Asn
                165                 170                 175

Gly Gln Ile Ile Met Leu Tyr Ser Gly Asn Ala Tyr Asp Leu Ser Gln
            180                 185                 190

Val Gln Cys Leu Ala Tyr Ala Val Asn Ser Ser Asp Pro Leu Leu Ile
        195                 200                 205

Glu Trp Lys Lys Tyr Glu Gly Asn Pro Val Leu Leu Pro Pro Pro Gly
    210                 215                 220

Val Gly Tyr Lys Asp Phe Arg Asp Pro Ser Thr Leu Trp Ser Gly Pro
225                 230                 235                 240

Asp Gly Glu Tyr Arg Met Val Met Gly Ser Lys His Asn Glu Thr Ile
                245                 250                 255

Gly Cys Ala Leu Ile Tyr His Thr Thr Asn Phe Thr His Phe Glu Leu
            260                 265                 270

Lys Glu Glu Val Leu His Ala Val Pro His Thr Gly Met Trp Glu Cys
        275                 280                 285

Val Asp Leu Tyr Pro Val Ser Thr Val His Thr Asn Gly Leu Asp Met
    290                 295                 300

Val Asp Asn Gly Pro Asn Val Lys Tyr Val Leu Lys Gln Ser Gly Asp
305                 310                 315                 320

Glu Asp Arg His Asp Trp Tyr Ala Ile Gly Ser Tyr Asp Ile Val Asn
```

|   |   |   |   |   | 325 |   |   |   |   | 330 |   |   |   |   | 335 |   |   |
|---|---|---|---|---|---|---|---|---|---|---|---|---|---|---|---|---|---|

Asp Lys Trp Tyr Pro Asp Asp Pro Glu Asn Asp Val Gly Ile Gly Leu
     340     345     350

Arg Tyr Asp Phe Gly Lys Phe Tyr Ala Ser Lys Thr Phe Tyr Asp Gln
   355     360     365

His Lys Lys Arg Arg Val Leu Trp Gly Tyr Val Gly Glu Thr Asp Pro
 370     375     380

Gln Lys Tyr Asp Leu Ser Lys Gly Trp Ala Asn Ile Leu Asn Ile Pro
385     390     395     400

Arg Thr Val Val Leu Asp Leu Glu Thr Lys Thr Asn Leu Ile Gln Trp
     405     410     415

Pro Ile Glu Glu Thr Glu Asn Leu Arg Ser Lys Lys Tyr Asp Glu Phe
    420     425     430

Lys Asp Val Glu Leu Arg Pro Gly Ala Leu Val Pro Leu Glu Ile Gly
   435     440     445

Thr Ala Thr Gln Leu Asp Ile Val Ala Thr Phe Glu Ile Asp Gln Lys
 450     455     460

Met Leu Glu Ser Thr Leu Glu Ala Asp Val Leu Phe Asn Cys Thr Thr
465     470     475     480

Ser Glu Gly Ser Val Ala Arg Ser Val Leu Gly Pro Phe Gly Val Val
    485     490     495

Val Leu Ala Asp Ala Gln Arg Ser Glu Gln Leu Pro Val Tyr Phe Tyr
   500     505     510

Ile Ala Lys Asp Ile Asp Gly Thr Ser Arg Thr Tyr Phe Cys Ala Asp
   515     520     525

Glu Thr Arg Ser Ser Lys Asp Val Ser Val Gly Lys Trp Val Tyr Gly
 530     535     540

Ser Ser Val Pro Val Leu Pro Gly Glu Lys Tyr Asn Met Arg Leu Leu
545     550     555     560

Val Asp His Ser Ile Val Glu Gly Phe Ala Gln Asn Gly Arg Thr Val
    565     570     575

Val Thr Ser Arg Val Tyr Pro Thr Lys Ala Ile Tyr Asn Ala Ala Lys
   580     585     590

Val Phe Leu Phe Asn Asn Ala Thr Gly Ile Ser Val Lys Ala Ser Ile
   595     600     605

Lys Ile Trp Lys Met Gly Glu Ala Glu Leu Asn Pro Phe Pro Leu Pro
610     615     620

Gly Trp Thr Phe Glu Leu
625     630

<210> SEQ ID NO 19
<211> LENGTH: 2115
<212> TYPE: DNA
<213> ORGANISM: Triticum aestivum

<400> SEQUENCE: 19

```
gggcttttca gcggaacaac aaccgaccgg tctcttccac ggcgcgagga ttaattggcg      60
gaggtcgctc cgccgcgcga gtacggcggg aggtcgtttt ccggcggagg aaaaagatgg     120
cgagcgaatc cagtcggcgg ggagattcaa cttcaactcg gaggcggagc ggacaagaac     180
ccctggctgt cctcgtctct gccaagaacc aatcctcctc cgaggagcgg gcaggggcg     240 gcctgcgggt cgacgaggag gccgcggccg ggttcccgtg gagcaacgag atgctgcagt     300
ggcagcgcag tggctaccat ttccagacgg ccaagaacta catgagcgat ccaacggtc     360 ttatgtacta caatggatgg taccacatgt tcttccagta caacccggtg ggcaccgatt     420
```

```
gggacgacgg catggagtgg ggccatgccg tgtctcggaa ccttgtcacg tggcgcaccc      480
tccctattgc catggtggct gaccagtggt acgacatcct gggggtcctt tcgggctcta      540
tgacggtgct accaaatggc acggtcatca tgatctacac gggggccacc aacgcctctg      600
ccgttgaggt gcagtgcatc gccacccccg ccgacgcccaa cgacccttc ctccgccgct      660 ggaccaagca ccccgccaac cccgtcatct ggtcgccgcc ggggatcggc accaaggatt      720
ttcgagaccc gatgactgct tggtacgatg aatctgatga cacatggcgc accctccttg      780
ggtccaagga tgaccacgac ggtcaccacg atgggatcgc catgatgtac aagaccaagg      840
acttccttaa ctacgagctc atcccgggta tcttgcatcg agtccagcgc accggcgagt      900
gggagtgcat tgacttctac cctgtcggcc acagaagcaa cgacaactca tcggagatgt      960
tgcacgtgtt gaaggcgagc atggacgacg aacggcacga ctactactcg ctaggcacgt     1020
acgactcggc agcaaacgcg tggacgccga tcgacccgga gctcgacttg gggatcgggc     1080
tgagatacga ctggggtaag ttttatgcgt ccacctcgtt ctatgatccg gcaaagaagc     1140
ggcgcgtgct gatggggtac gtcggcgagg tcgactccaa gcgggctgat gtcgtgaagg     1200
gatgggcctc gattcagtca gttccaagga caattgctct cgacgagaag acccggacga     1260
acctcctcct ctggcccgtg gaggagattg agaccctccg cctcaacgcc accgaactta     1320
gcgacgtcac ccttaacacc ggctccgtca tccatatccc gctccgccaa ggcactcagc     1380
tcgacatcga ggcaactttc caccttgatg cttctgccgt cgctgccctc aatgaggccg     1440
atgtgggcta caactgcagc agcagcgcg gtgctgttaa ccgcggcgcg ctaggcccct     1500
tcggcctcct cgtcctcgct gctggtgacc gccgtggcga gcaaacggcg gtgtatttct     1560
acgtgtctag ggggctcgac ggaggcctcc ataccagctt ctgccaagac gagttgcggt     1620
cgtcacgggc caaggatgtg acgaagcggg tgattgggag cacggtgccg gtgctcgacg     1680
gcgaggcttt ctcgatgagg gtgctcgtgg accactccat cgtgcagggc ttcgcgatgg     1740
gcgggaggac cacgatgacg tcgcgggtgt acccgatgga ggcctatcag gaggcaaaag     1800
tgtacttgtt caacaatgcg accggtgcca gcgtcatggc ggaaaggctc gtcgtgcacg     1860
agatggactc agcacacaac cagctctcca atatggacga tcactcgtat gttcaatgaa     1920
gctcttgcat ctcatcagta ataagctaca ttggatcaaa gacgcgcacc aaggaaggcc     1980
aagacatatg taaatgattc cgcacagcct cgcttgcaga attgaaacat ctatccttgg     2040
gtcatgttct gcattgatgt cactgtgaac tacagtatat tactttgttg ggcgtagaaa     2100
aaaaaaaaaa aaaaa                                                     2115
```

```
<210> SEQ ID NO 20
<211> LENGTH: 600
<212> TYPE: PRT
<213> ORGANISM: Triticum aestivum

<400> SEQUENCE: 20

Met Ala Ser Glu Ser Ser Arg Arg Gly Asp Ser Thr Ser Thr Arg Arg
 1               5                  10                  15

Arg Ser Gly Gln Glu Pro Leu Ala Val Leu Val Ser Ala Lys Asn Gln
                20                  25                  30

Ser Ser Ser Glu Glu Arg Ala Gly Gly Gly Leu Arg Val Asp Glu Glu
            35                  40                  45

Ala Ala Ala Gly Phe Pro Trp Ser Asn Glu Met Leu Gln Trp Gln Arg
        50                  55                  60

Ser Gly Tyr His Phe Gln Thr Ala Lys Asn Tyr Met Ser Asp Pro Asn
```

```
             65                  70                  75                  80
Gly Leu Met Tyr Tyr Asn Gly Trp Tyr His Met Phe Phe Gln Tyr Asn
                         85                  90                  95
Pro Val Gly Thr Asp Trp Asp Gly Met Glu Trp Gly His Ala Val
                100                 105                 110
Ser Arg Asn Leu Val Thr Trp Arg Thr Leu Pro Ile Ala Met Val Ala
                115                 120                 125
Asp Gln Trp Tyr Asp Ile Leu Gly Val Leu Ser Gly Ser Met Thr Val
                130                 135                 140
Leu Pro Asn Gly Thr Val Ile Met Ile Tyr Thr Gly Ala Thr Asn Ala
145                 150                 155                 160
Ser Ala Val Glu Val Gln Cys Ile Ala Thr Pro Ala Asp Pro Asn Asp
                165                 170                 175
Pro Phe Leu Arg Arg Trp Thr Lys His Pro Ala Asn Pro Val Ile Trp
                180                 185                 190
Ser Pro Pro Gly Ile Gly Thr Lys Asp Phe Arg Asp Pro Met Thr Ala
                195                 200                 205
Trp Tyr Asp Glu Ser Asp Asp Thr Trp Arg Thr Leu Leu Gly Ser Lys
                210                 215                 220
Asp Asp His Asp Gly His His Asp Gly Ile Ala Met Met Tyr Lys Thr
225                 230                 235                 240
Lys Asp Phe Leu Asn Tyr Glu Leu Ile Pro Gly Ile Leu His Arg Val
                245                 250                 255
Gln Arg Thr Gly Glu Trp Glu Cys Ile Asp Phe Tyr Pro Val Gly His
                260                 265                 270
Arg Ser Asn Asp Asn Ser Ser Glu Met Leu His Val Leu Lys Ala Ser
                275                 280                 285
Met Asp Asp Glu Arg His Asp Tyr Tyr Ser Leu Gly Thr Tyr Asp Ser
                290                 295                 300
Ala Ala Asn Ala Trp Thr Pro Ile Asp Pro Glu Leu Asp Leu Gly Ile
305                 310                 315                 320
Gly Leu Arg Tyr Asp Trp Gly Lys Phe Tyr Ala Ser Thr Ser Phe Tyr
                325                 330                 335
Asp Pro Ala Lys Lys Arg Arg Val Leu Met Gly Tyr Val Gly Glu Val
                340                 345                 350
Asp Ser Lys Arg Ala Asp Val Val Lys Gly Trp Ala Ser Ile Gln Ser
                355                 360                 365
Val Pro Arg Thr Ile Ala Leu Asp Glu Lys Thr Arg Thr Asn Leu Leu
                370                 375                 380
Leu Trp Pro Val Glu Glu Ile Glu Thr Leu Arg Leu Asn Ala Thr Glu
385                 390                 395                 400
Leu Ser Asp Val Thr Leu Asn Thr Gly Ser Val Ile His Ile Pro Leu
                405                 410                 415
Arg Gln Gly Thr Gln Leu Asp Ile Glu Ala Thr Phe His Leu Asp Ala
                420                 425                 430
Ser Ala Val Ala Ala Leu Asn Glu Ala Asp Val Gly Tyr Asn Cys Ser
                435                 440                 445
Ser Ser Gly Gly Ala Val Asn Arg Gly Ala Leu Gly Pro Phe Gly Leu
                450                 455                 460
Leu Val Leu Ala Ala Gly Asp Arg Arg Gly Glu Gln Thr Ala Val Tyr
465                 470                 475                 480
Phe Tyr Val Ser Arg Gly Leu Asp Gly Gly Leu His Thr Ser Phe Cys
                485                 490                 495
```

```
Gln Asp Glu Leu Arg Ser Ser Arg Ala Lys Asp Val Thr Lys Arg Val
            500                 505                 510

Ile Gly Ser Thr Val Pro Val Leu Asp Gly Glu Ala Phe Ser Met Arg
        515                 520                 525

Val Leu Val Asp His Ser Ile Val Gln Gly Phe Ala Met Gly Gly Arg
    530                 535                 540

Thr Thr Met Thr Ser Arg Val Tyr Pro Met Glu Ala Tyr Gln Glu Ala
545                 550                 555                 560

Lys Val Tyr Leu Phe Asn Asn Ala Thr Gly Ala Ser Val Met Ala Glu
                565                 570                 575

Arg Leu Val Val His Glu Met Asp Ser Ala His Asn Gln Leu Ser Asn
                580                 585                 590

Met Asp Asp His Ser Tyr Val Gln
            595                 600

<210> SEQ ID NO 21
<211> LENGTH: 625
<212> TYPE: PRT
<213> ORGANISM: Hordeum vulgare

<400> SEQUENCE: 21

Met Gly Ser His Gly Lys Pro Pro Leu Pro Tyr Ala Tyr Lys Pro Leu
  1               5                  10                  15

Pro Ser Asp Ala Ala Asp Gly Lys Arg Thr Gly Cys Met Arg Trp Ser
             20                  25                  30

Ala Cys Ala Thr Val Leu Thr Ala Ser Ala Met Ala Val Val Val Val
         35                  40                  45

Gly Ala Thr Leu Leu Ala Gly Leu Arg Met Glu Gln Ala Val Asp Glu
     50                  55                  60

Glu Ala Ala Ala Gly Gly Phe Pro Trp Ser Asn Glu Met Leu Gln Trp
 65                  70                  75                  80

Gln Arg Ser Gly Tyr His Phe Gln Thr Ala Lys Asn Tyr Met Ser Asp
                 85                  90                  95

Pro Asn Gly Leu Met Tyr Tyr Arg Gly Trp Tyr His Met Phe Tyr Gln
            100                 105                 110

Tyr Asn Pro Val Gly Thr Asp Trp Asp Asp Gly Met Glu Trp Gly His
        115                 120                 125

Ala Val Ser Arg Asn Leu Val Gln Trp Arg Thr Leu Pro Ile Ala Met
    130                 135                 140

Val Ala Asp Gln Trp Tyr Asp Ile Leu Gly Val Leu Ser Gly Ser Met
145                 150                 155                 160

Thr Val Leu Pro Asn Gly Thr Val Ile Met Ile Tyr Thr Gly Ala Thr
                165                 170                 175

Asn Ala Ser Ala Val Glu Val Gln Cys Ile Ala Thr Pro Ala Asp Pro
            180                 185                 190

Asn Asp Pro Leu Leu Arg Arg Trp Thr Lys His Pro Ala Asn Pro Val
        195                 200                 205

Ile Trp Ser Pro Pro Gly Val Gly Thr Lys Asp Phe Arg Asp Pro Met
    210                 215                 220

Thr Ala Trp Tyr Asp Glu Ser Asp Glu Thr Trp Arg Thr Leu Leu Gly
225                 230                 235                 240

Ser Lys Asp Asp His Asp Gly His His Asp Gly Ile Ala Met Met Tyr
                245                 250                 255

Lys Thr Lys Asp Phe Leu Asn Tyr Glu Leu Ile Pro Gly Ile Leu His
            260                 265                 270
```

-continued

```
Arg Val Val Arg Thr Gly Glu Trp Glu Cys Ile Asp Phe Tyr Pro Val
        275                 280                 285
Gly Arg Arg Ser Ser Asp Asn Ser Ser Glu Met Leu His Val Leu Lys
        290                 295                 300
Ala Ser Met Asp Asp Glu Arg His Asp Tyr Tyr Ser Leu Gly Thr Tyr
305                 310                 315                 320
Asp Ser Ala Ala Asn Thr Trp Thr Pro Ile Asp Pro Glu Leu Asp Leu
                325                 330                 335
Gly Ile Gly Leu Arg Tyr Asp Trp Gly Lys Phe Tyr Ala Ser Thr Ser
                340                 345                 350
Phe Tyr Asp Pro Ala Lys Asn Arg Arg Val Leu Met Gly Tyr Val Gly
                355                 360                 365
Glu Val Asp Ser Lys Arg Ala Asp Val Val Lys Gly Trp Ala Ser Ile
370                 375                 380
Gln Ser Val Pro Arg Thr Val Ala Leu Asp Glu Lys Thr Arg Thr Asn
385                 390                 395                 400
Leu Leu Leu Trp Pro Val Glu Glu Ile Glu Thr Leu Arg Leu Asn Ala
                405                 410                 415
Thr Glu Leu Thr Asp Val Thr Ile Asn Thr Gly Ser Val Ile His Ile
                420                 425                 430
Pro Leu Arg Gln Gly Thr Gln Leu Asp Ile Glu Ala Ser Phe His Leu
                435                 440                 445
Asp Ala Ser Ala Val Ala Ala Leu Asn Glu Ala Asp Val Gly Tyr Asn
450                 455                 460
Cys Ser Ser Ser Gly Gly Ala Val Asn Arg Gly Ala Leu Gly Pro Phe
465                 470                 475                 480
Gly Leu Leu Val Leu Ala Ala Gly Asp Arg Arg Gly Glu Gln Thr Ala
                485                 490                 495
Val Tyr Phe Tyr Val Ser Arg Gly Leu Asp Gly Gly Leu His Thr Ser
                500                 505                 510
Phe Cys Gln Asp Glu Leu Arg Ser Ser Arg Ala Lys Asp Val Thr Lys
        515                 520                 525
Arg Val Ile Gly Ser Thr Val Pro Val Leu Asp Gly Glu Ala Leu Ser
        530                 535                 540
Met Arg Val Leu Val Asp His Ser Ile Val Gln Gly Phe Asp Met Gly
545                 550                 555                 560
Gly Arg Thr Thr Met Thr Ser Arg Val Tyr Pro Met Glu Ser Tyr Gln
                565                 570                 575
Glu Ala Arg Val Tyr Leu Phe Asn Asn Ala Thr Gly Ala Ser Val Thr
                580                 585                 590
Ala Glu Arg Leu Val Val His Glu Met Asp Ser Ala His Asn Gln Leu
                595                 600                 605
Ser Asn Glu Asp Asp Gly Met Tyr Leu His Gln Val Leu Glu Ser Arg
        610                 615                 620
His
625
```

FRUCTAN BIOSYNTHETIC ENZYMES

This application is Divisonal of U.S. application Ser. No. 13/011,345, filed Jan. 21, 2011, now U.S. Pat. No. 8,168,862, issued May 1, 2012, which is a Continuation of U.S. application Ser. No. 11/930,552, filed Oct. 31, 2007, now U.S. Pat. No. 7,875,763, issued Jan. 25, 2011, which is a Continuation of U.S. application Ser. No. 11,780,546, filed Jul. 20, 2007, now U.S. Pat. No. 7,803,986, issued Sep. 28, 2010, which is a Continuation of U.S. application Ser. No. 10/916,247, filed Aug. 11, 2004, now U.S. Pat. No. 7,253,335, issued Aug. 7, 2007, which is a Divisional of U.S. application Ser. No. 10/003,392, filed Oct. 30, 2001, now U.S. Pat. No. 6,791,015, issued Sep. 14, 2004, which claims the benefit of U.S. Provisional Application No. 60/244,273, filed Oct. 30, 2000, and U.S. Provisional Application No. 60/269,543, filed Feb. 16, 2001. The entire contents of these applications are herein incorporated by reference.

FIELD OF THE INVENTION

This invention is in the field of plant molecular biology. More specifically, this invention pertains to nucleic acid fragments encoding fructosyltransferases in plants and seeds.

BACKGROUND OF THE INVENTION

Fructans are linear or branched polymers of repeating fructose residues with usually one terminal glucose unit. The number of residues contained in an individual polymer, also known as the degree of polymerization (DP), varies greatly depending on the source from which the polymer is isolated. Several bacteria can produce fructans with a DP 5000 or greater, while low DP fructans (DP 3 to 200) are found in over 40,000 plant species.

Based on their structure, several types of fructans can be identified in higher plants. The most characterized plant fructan is inulin. Inulin contains linear β(2-1)-linked fructosyl residues and commonly occurs in the *Asterales* such as Jerusalem artichoke (*Helianthus tuberosus*), sunflower (*Helianthus* sp.), Belgian endive (*Cichorium intybus*) and artichoke (*Cynara scolymus*). Inulin synthesis is initiated by sucrose:sucrose 1-fructosyltransferase (1-SST; EC 2.4.1.99) which catalyses the conversion of sucrose into isokestose (also named 1-kestose) and glucose. Additional fructosyl units are added onto isokestose, by the action of a fructan: fructan 1-fructosyltransferase (1-FFT, EC 2.4.1.100) resulting in a β(2-1)-linked fructose oligomer.

A second type of fructan is called levan and consists of linear β(2-6) linked fructosyl residues. Grasses such as *Dactylis glomerata* and *Phleum pratense* contain levans with a DP up to 200. Levans are synthesized by a sucrose:fructan 6-fructosyltransferase (6-SFT; EC 2.4.1.10) that uses sucrose as a fructosyl donor and acceptor to produce 6-kestose. Polymerization of 6-kestose is believed to be catalyzed by 6-SFT as well, using sucrose as the fructosyl donor.

A third type of fructan, graminan (also called mixed-levan), is found in many *Poales* such as barley and wheat. These plants use an SST to produce iso-kestose from sucrose, and 6-SFT to further polymerize isokestose, resulting in a fructan containing both the β(2-1) and the β(2-6) linked fructosyl residues.

The fourth type of fructan is often referred to as the neo-kestose series of fructans. The neo-kestose series have fructosyl residues on the carbon 1 and 6 of glucose producing a polymer with fructosyl residues on either end of the sucrose molecule. The inulin-neoseries found in *Liliales* such as onion (*Allium cepa*), leek (*Allium porrum*), and asparagus (*Asparagus officinales*) contain mainly a β(2-1)-linked fructose polymer linked to carbon 1 and 6 of glucose, while the levan-neoseries contain mainly a β(2-6)-linked fructose polymer linked to carbon 1 and 6 of glucose. Neoseries fructans are believed to be synthesized by the concerted action of 1-SST (producing isokestose) and 6G-FFT, a specific fructan: fructan 6G-fructosyltransferase that polymerizes fructosyl units onto carbon 6 of glucose.

Industrial applications of fructans are very diverse and range from medical, food, and feed applications, as well as the use of fructans as a raw material for the production of industrial polymers and high-fructose syrup. Regardless of size, fructose polymers are not metabolized by humans and animals. Fructans can enhance animal health and performance by being selectively fermented by beneficial organisms such as *Bifidibacterium* in the large intestine of animals, at the expense of pathogenic organisms such as *E. coli* and *Salmonella*, leading to altered fatty acid profiles, increased nutrient absorption, and decreased levels of blood cholesterol. Also, fructans have a sweet taste and are increasingly used as low-calorie sweeteners and as functional food ingredients.

Accordingly, there is a great deal of interest in understanding fructan biosynthetic pathways. With the isolation of nucleic acid fragments encoding various enzymes involved in the pathway, it may be possible to engineer transgenic plants to produce desired levels of different types of useful and novel fructans.

SUMMARY OF THE INVENTION

The present invention concerns an isolated polynucleotide comprising: (a) a first nucleotide sequence encoding a first polypeptide comprising at least 58 amino acids, wherein the amino acid sequence of the first polypeptide and the amino acid sequence of SEQ ID NO:12 have at least 90% or 95% identity based on the Clustal alignment method, (b) a second nucleotide sequence encoding a second polypeptide comprising at least 140 amino acids, wherein the amino acid sequence of the second polypeptide and the amino acid sequence of SEQ ID NO:6 have at least 90% or 95% identity based on the Clustal alignment method, (c) a third nucleotide sequence encoding a third polypeptide comprising at least 471 amino acids, wherein the amino acid sequence of the third polypeptide and the amino acid sequence of SEQ ID NO:10 have at least 95% identity based on the Clustal alignment method, (d) a fourth nucleotide sequence encoding a fourth polypeptide comprising at least 495 amino acids, wherein the amino acid sequence of the fourth polypeptide and the amino acid sequence of SEQ ID NO:8 have at least 95% identity based on the Clustal alignment method, (e) a fifth nucleotide sequence encoding a fifth polypeptide comprising at least 600 amino acids, wherein the amino acid sequence of the fifth polypeptide and the amino acid sequence of SEQ ID NO:2 have at least 85%, 90%, or 95% identity based on the Clustal alignment method, (f) a sixth nucleotide sequence encoding a sixth polypeptide comprising at least 600 amino acids, wherein the amino acid sequence of the sixth polypeptide and the amino acid sequence of SEQ ID NO:4 or SEQ ID NO:14 have at least 90% or 95% identity based on the Clustal alignment method, (g) a seventh nucleotide sequence encoding a seventh polypeptide comprising at least 630 amino acids, wherein the amino acid sequence of the seventh polypeptide and the amino acid sequence of SEQ ID NO:16 have at least 97% identity based on the Clustal alignment method, or (h) the complement of the first, second, third, fourth, fifth, sixth, or seventh nucleotide sequence, wherein the complement and the first, second, third, fourth, fifth, sixth, or seventh nucleotide sequence contain the same number of nucleotides and are 100% complementary.

In a second embodiment, the first polypeptide preferably comprises the amino acid sequence of SEQ ID NO:12, the second polypeptide preferably comprises the amino acid sequence of SEQ ID NO:6, the third polypeptide preferably comprises the amino acid sequence of SEQ ID NO:10, the fourth polypeptide preferably comprises the amino acid sequence of SEQ ID NO:8, the fifth polypeptide preferably comprises the amino acid sequence of SEQ ID NO:2, the sixth polypeptide preferably comprises the amino acid sequence of SEQ ID NO:4 or SEQ ID NO:14, and the seventh polypeptide preferably comprises the amino acid sequence of SEQ ID NO:16.

In a third embodiment, the first nucleotide sequence preferably comprises the nucleotide sequence of SEQ ID NO:11, the second nucleotide sequence preferably comprises the nucleotide sequence of SEQ ID NO:5, the third nucleotide sequence preferably comprises the nucleotide sequence of SEQ ID NO:9, the fourth nucleotide sequence preferably comprises the nucleotide sequence of SEQ ID NO:7, the fifth nucleotide sequence preferably comprises the nucleotide sequence of SEQ ID NO:1, the sixth nucleotide sequence preferably comprises the nucleotide sequence of SEQ ID NO:3 or SEQ ID NO:13, and the seventh nucleotide sequence preferably comprises the nucleotide sequence of SEQ ID NO:15.

In a fourth embodiment, the first, second, third, fourth, fifth, sixth, and seventh polypeptides preferably are fructosyltranferases.

In a fifth embodiment, the first, third and fourth polypeptides preferably are 6-SFT, the second and fifth polypeptides preferably are 1-FFT, the sixth polypeptide preferably is 1-FFT or 1-SST, and the seventh polypeptide preferably is 1-SST.

In a sixth embodiment, this invention relates to a vector comprising the polynucleotide of the present invention, or to a recombinant DNA construct comprising the polynucleotide of the present invention operably linked to at least one regulatory sequence. The invention includes a cell, a plant, or a seed comprising the recombinant DNA construct of the present invention. The cell may be a eukaryotic cell such as a plant cell, or a prokaryotic cell such as a bacterial cell.

In a seventh embodiment, the invention relates to a virus, preferably a baculovirus, comprising an isolated polynucleotide of the present invention or a recombinant DNA construct of the present invention.

In an eighth embodiment, the invention relates to a method of transforming a cell by introducing into the cell a nucleic acid comprising a polynucleotide of the present invention. The invention also concerns a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a ninth embodiment, the present invention relates to (a) a method for producing a polynucleotide fragment comprising selecting a nucleotide sequence comprised by any of the polynucleotides of the present invention, wherein the selected nucleotide sequence contains at least 30, 40, or 60 nucleotides, and synthesizing a polynucleotide fragment containing the selected nucleotide sequence, and (b) the polynucleotide fragment produced by this method.

In a tenth embodiment, the present invention relates to an isolated polynucleotide fragment comprising a nucleotide sequence comprised by any of the polynucleotides of the present invention, wherein the nucleotide sequence contains at least 30, 40, or 60 nucleotides, and a cell, a plant, and a seed comprising the isolated polynucleotide.

In an eleventh embodiment, the present invention concerns an isolated polypeptide comprising: (a) a first amino acid sequence comprising at least 58 amino acids, wherein the first amino acid sequence and the amino acid sequence of SEQ ID NO:12 have at least 90% or 95% identity based on the Clustal alignment method, (b) a second amino acid sequence comprising at least 140 amino acids, wherein the second amino acid sequence and the amino acid sequence of SEQ ID NO:6 have at least 90% or 95% identity based on the Clustal alignment method, (c) a third amino acid sequence encoding comprising at least 471 amino acids, wherein the third amino acid sequence and the amino acid sequence of SEQ ID NO:10 have at least 95% identity based on the Clustal alignment method, (d) a fourth amino acid sequence comprising at least 495 amino acids, wherein the fourth amino acid sequence and the amino acid sequence of SEQ ID NO:8 have at least 95% identity based on the Clustal alignment method, (e) a fifth amino acid sequence comprising at least 600 amino acids, wherein the fifth amino acid sequence and the amino acid sequence of SEQ ID NO:2 have at least 85%, 90%, or 95% identity based on the Clustal alignment method, (f) a sixth amino acid sequence comprising at least 600 amino acids, wherein the sixth amino acid sequence and the amino acid sequence of SEQ ID NO:4 or SEQ ID NO:14 have at least 90% or 95% identity based on the Clustal alignment method, or (g) a seventh amino acid sequence comprising at least 630 amino acids, wherein the seventh amino acid sequence and the amino acid sequence of SEQ ID NO:16 have at least 97% identity based on the Clustal alignment method. The first amino acid sequence preferably comprises the amino acid sequence of SEQ ID NO:12, the second amino acid sequence preferably comprises the amino acid sequence of SEQ ID NO:6, the third amino acid sequence preferably comprises the amino acid sequence of SEQ ID NO:10, the fourth amino acid sequence preferably comprises the amino acid sequence of SEQ ID NO:8, the fifth amino acid sequence preferably comprises the amino acid sequence of SEQ ID NO:2, the sixth amino acid sequence preferably comprises the amino acid sequence of SEQ ID NO:4 or SEQ ID NO:14, and the seventh amino acid sequence preferably comprises the amino acid sequence of SEQ ID NO:16. The polypeptide preferably is a fructosyltranferase. The first, third and fourth amino acid sequences preferably are 6-SFT, the second and fifth amino acid sequences preferably are 1-FFT, the sixth amino acid sequence preferably is 1-FFT or 1-SST, and the seventh amino acid sequence preferably is 1-SST.

In a twelfth embodiment, the invention concerns a method for isolating a polypeptide encoded by the polynucleotide of the present invention comprising isolating the polypeptide from a cell containing a recombinant DNA construct comprising the polynucleotide operably linked to a regulatory sequence.

In a thirteenth embodiment, the invention relates to a method of selecting an isolated polynucleotide that affects the level of expression of a fructan biosynthetic enzyme (fructosyltransferase) polypeptide or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the fructan biosynthetic enzyme (fructosyltransferase) polypeptide or enzyme activity in the host cell containing the isolated polynucleotide or the isolated recombinant DNA construct; and (d) comparing the level of the fructan biosynthetic enzyme (fructosyltransferase) polypeptide or enzyme activity in the host cell containing the isolated polynucleotide or the isolated recombinant DNA construct with the level of the fructan biosynthetic enzyme (fructosyltransferase) polypeptide or enzyme activity in the host cell that does not contain the isolated polynucleotide or the isolated recombinant DNA construct.

In a fourteenth embodiment, the invention concerns a method of obtaining a nucleic acid fragment encoding a substantial portion of a fructan biosynthetic enzyme (fructosyltransferase) polypeptide, preferably a plant fructan biosynthetic enzyme (fructosyltransferase) polypeptide, comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NOs:1, 3, 5, 7, 9, 11, 13, and 15 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a fructan biosynthetic enzyme (fructosyltransferase) polypeptide amino acid sequence.

In a fifteenth embodiment, this invention relates to a method of obtaining a nucleic acid fragment encoding all or a substantial portion of the amino acid sequence encoding a fructan biosynthetic enzyme (fructosyltransferase) polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a sixteenth embodiment, this invention concerns a composition, such as a hybridization mixture, comprising an isolated polynucleotide of the present invention.

In a seventeenth embodiment, this invention concerns a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the fructan biosynthetic enzyme (fructosyltransferase) polypeptide in an amount sufficient to complement a null mutant to provide a positive selection means.

In an eighteenth embodiment, this invention relates to a method of altering the level of expression of a fructan biosynthetic enzyme (fructosyltransferase) polypeptide in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the fructan biosynthetic enzyme (fructosyltransferase) polypeptide in the transformed host cell.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A-1C show an alignment of the 1-FFT amino acid sequences encoded by the African daisy clone dms2c.pk006.p1 (SEQ ID NO:2), the guayule clone epb3c.pk007.j9 (SEQ ID NO:4), and the sunflower clone hss1c.pk004.15 (SEQ ID NO:6), with the *Helianthus tuberosus* 1-FFT (NCBI General Identifier No. 3367690; SEQ ID NO:17). Amino acids conserved among all sequences are indicated with an asterisk (*) above the alignment. The program uses dashes to maximize the alignment. FIG. 1A shows amino acids 1 through 240, FIG. 1B shows amino acids 241 through 480, and FIG. 1C shows amino acids 481 through 624.

FIGS. 2A-2C shows an alignment of the 6-SFT amino acid sequences encoded by by the wheat clone wdk1c.pk014.c11 (SEQ ID NO:8), wheat clone wdk2c.pk017.f14 (SEQ ID NO:10), wheat clone wr1.pk0085.h8 (SEQ ID NO:12), and wheat clone wdk2c.pk017.f14:cgs (SEQ ID NO:20), with the *Hordeum vulgare* sequence (NCBI General Identifier No. 7435467; SEQ ID NO:21). Amino acids conserved among all sequences are indicated with an asterisk (*) above the alignment. The program uses dashes to maximize the alignment. FIG. 2A shows amino acids 1 through 240, FIG. 2B shows amino acids 241 through 480, and FIG. 2C shows amino acids 481 through 625.

FIGS. 3A-3B show an alignment of the 1-SST amino acid sequences encoded by the guayule clone epb3c.pk007.n11 (SEQ ID NO:14) and the sunflower clone hhs1c.pk004.e5 (SEQ ID NO:16), with the Helianthus tuberosus 1-SST (NCBI General Identifier No. 3367711; SEQ ID NO:18). Amino acids conserved among all sequences are indicated with an asterisk (*) above the alignment. The program uses dashes to maximize the alignment. FIG. 3A shows amino acids 1 through 350, and FIG. 3B shows amino acids 351 through 637.

Table 1 lists the polypeptides that are described herein (including the plant source from where they are derived), the designation of the cDNA clones that comprise the nucleic acid fragments encoding polypeptides representing all or a substantial portion of these polypeptides, and the corresponding identifier (SEQ ID NO:) as used in the attached Sequence Listing. The table also includes the art sequences used in the figures, the polypeptide, source, and General Identifier No. (GI No.). The sequence descriptions and Sequence Listing attached hereto comply with the rules governing nucleotide and/or amino acid sequence disclosures in patent applications as set forth in 37 C.F.R. §1.821-1.825.

TABLE 1

| | Fructosyltransferases | | |
|---|---|---|---|
| | | SEQ ID NO: | |
| Protein | Clone Designation | (Nucleotide) | (Amino Acid) |
| African Daisy 1-FFT | dms2c.pk006.p1 | 1 | 2 |
| Guayule 1-FFT | epb3c.pk007.j9 | 3 | 4 |
| Sunflower 1-FFT | hss1c.pk004.i5:fis | 5 | 6 |
| Wheat 6-SFT | wdk1c.pk014.c11 | 7 | 8 |
| Wheat 6-SFT | wdk2c.pk017.f14 | 9 | 10 |
| Wheat 6-SFT | wr1.pk0085.h8 | 11 | 12 |
| Guayule 1-SST | epb3c.pk007.n11 | 13 | 14 |
| Sunflower 1-SST | hhs1c.pk004.e5 | 15 | 16 |
| *H. tuberosus* 1-FFT | GI No. 3367690 | | 17 |
| *H. tuberosus* 1-SST | GI No. 3367711 | | 18 |
| Wheat 6-SFT | wdk2c.pk017.f14:cgs | 19 | 20 |
| *Hordeum vulgare* 6-SFT | GI No. 7435467 | | 21 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 13, 15, or 19 or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not alter the functional properties of the polypeptide encoded by the nucleotide sequence. "Substantially similar" also refers to nucleic acid fragments wherein changes in one or more nucleotide bases does not change the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 13, or 15 and the complement of such nucleotide sequences may be used to affect the expression and/or function of a fructosyltransferase selected from 1-FFT, 6-SFT and 1-SST in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. The amino acid sequences may be 96% identical, 97% identical, 98% identical, 99% identical, or any integer thereof. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) $CABIOS$. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) $J. Mol. Biol.$ 215:403-410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that because in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by effecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising a nucleotide sequence encoding a polypeptide having fructosyltransferase activity wherein (a) the amino acid sequence of the polypeptide and the amino acid sequence of SEQ ID NO:2, 4, or 6 have at least 90% sequence identity; (b) the amino acid sequence of the polypeptide and the amino acid sequence of SEQ ID NO:14 or 16 have at least 97% identity. It is preferred that the identity in (a) be at least 95%. The present invention also relates to isolated polynucleotides comprising the complement of the nucleotide sequence, wherein the complement and the nucleotide sequence contain the same number of nucleotides and are 100% complementary. More specifically, the present invention concerns isolated polynucleotides encoding 1-FFT polypeptides having the sequence of SEQ ID NO:2, 4, or 6, or 1-SST polypeptides having the sequence of SEQ ID NO:14 or 16.

Nucleic acid fragments encoding at least a portion of several fructosyltransferases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other 1-FFTs, 6-SFTs, or 1-SSTs, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 13, or 15 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the fructan profile in those cells. Nucleic acid fragments encoding the fructan biosynthetic enzymes (fructosyltransferases) disclosed herein may be used to generate trangenic plants that produce particular fructans. In particular, the ability to produce fructans of the desired size in large amounts in crops of agronomic importance, such as corn or soybean, will reduce fructan production costs.

U.S. Pat. No. 5,840,361 teaches the health benefits of baby food compositions comprising fructan-containing vegetables. These benefits are based on the role of fructan-containing foods in stimulating the production of beneficial intestinal microbes, such as the *Bifidobacterium* species. Bifidobacteria are thought to promote health by their fermentation of sugars in the colon. This activity inhibits the development of putrefactive bacteria and provides resistance to infective gastroenteritis (Langhendries et al. (1995) *J Ped Gastroenterol Nutr* 21:177-181; Jason et al. (1984) *Pediatrics* 74(Suppl):702-727; Howie et al. (1990) *Br Med J* 300:11-16). Stimulating colonic bifidobacteria may also result in the enhancement of immune functions, the improvement of digestion and absorption of essential nutrients, and the synthesis of vitamins (Gibson et al. (1995) *J Nutr* 125:1401-1412). One approach to increasing the colonic bifidobacteria in humans is termed prebiotics. Prebiotics involves feeding of a nondigestable food ingredient, such as fructooligosaccharides, that beneficially affects the microflora by selectively stimulating the growth and/or activity of beneficial bacteria. Oral administration to humans of fructans such as oligofructose and inulin have been shown to increase the number of bifidobacteria in stools (Gibson et al. (1995) *Gastroenterol* 108:975-982). Consequently, fructans have been recommended as dietary supplements to adult humans (Modler et al. (1990) *Can Inst Food Sci Technol J* 23:29-41). The enzymes 1-SST and 1-FFT are involved in the biosynthesis of inulin and other fructans. The overexpression of 1-SST and 1-FFT in crop species such as corn, wheat, rice and soybean should facilitate the production of fructan-containing material with beneficial prebiotic properties.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by amplification of DNA or RNA, Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the recombinant DNA fragments described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a fructosyltransferase polypeptide, most preferably a 1-FFT polypeptide having an amino acid sequence that is at least 90% identical, based on the Clustal method of alignment, to a polypeptide selected from the group consisting of SEQ ID NOs:2, 4, and 6. The preferred fructosyltransferase polypeptide may be a 1-SST polypeptide having an amino acid sequence that is at least 97% identical, based on the Clustal method of alignment, to a polypeptide selected from the group consisting of SEQ ID NOs:14 and 16.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded fructosyltransferase (1-FFT, 6-SFT, or 1-SST). An example of a vector for high level expression of the instant polypeptides in a bacterial host is provided (Example 8).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various African daisy (*Dimorphotheca sinuata*), guayule (*Parthenium argentatum* Grey), sunflower (*Helianthus* sp.), and wheat (*Triticum aestivum*) tissues were prepared. The general characteristics of the libraries are indicated below.

TABLE 2 cDNA Libraries from African Daisy, Guayule, Sunflower, and Wheat

| Library | Tissue | Clone |
| --- | --- | --- |
| dms2c | African Daisy Developing Seed | dms2c.pk006.p1 |
| epb3c | Guayule Stem Bark | epb3c.pk007.j9<br>epb3c.pk007.n11 |
| hhs1c | Sunflower Head Tissue Infected With Sclerotinia | hhs1c.pk004.e5 |
| hss1c | Sclerotinia-Infected Sunflower Plant | hss1c.pk004.i5 |
| wdk1c | Wheat Developing Kernel, 3 Days After Anthesis | wdk1c.pk014.c11 |
| wdk2c | Wheat Developing Kernel, 7 Days After Anthesis | wdk2c.pk017.f14<br>wdk2c.pk017.f14:cgs |
| wr1 | Wheat Root From 7 Day Old Seedling | wr1.pk0085.h8 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding fructosyltransferases (1-FFT, 6-SFT, or 1-SST) were identified by conducting BLAST (Basic Local Alignment Search Tool; Altschul et al. (1993) *J. Mol. Biol.* 215:403-410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding 1-FFT

The BLASTX search using the EST sequences from clones listed in Table 3 revealed similarity of the polypeptides encoded by the cDNAs to 1-FFT from *Helianthus tuberosus* (NCBI General Identifier No. 3367690). Shown in Table 3 are the BLAST results for individual ESTs ("EST"), or for the sequences of the entire cDNA inserts comprising the indicated cDNA clones ("FIS") and encoding the entire protein ("CGS"):

TABLE 3

BLAST Results for Sequences Encoding Polypeptides Homologous to 1-FFT

| Clone | Status | BLAST pLog Score NCBI GI No. 3367690 |
|---|---|---|
| dms2c.pk006.p1:fis | CGS | >180.00 |
| epb3c.pk007.j9:fis | CGS | >180.00 |
| hss1c.pk004.i5 | EST | 83.70 |

The nucleotide sequence of the entire cDNA insert in clone dms2c.pk006.p1 is shown in SEQ ID NO:1. The amino acid sequence deduced from nucleotides 33 through 1856 of SEQ ID NO:1 is shown in SEQ ID NO:2. The nucleotide sequence of the entire cDNA insert in clone epb3c.pk007.j9 is shown in SEQ ID NO:3. The amino acid sequence deduced from nucleotides 63 through 1889 of SEQ ID NO:3 is shown in SEQ ID NO:4. The nucleotide sequence of a portion of the cDNA insert in clone hss1c.pk004.15 is shown in SEQ ID NO:5. The amino acid sequence deduced from nucleotides 1 through 413 of SEQ ID NO:5 is shown in SEQ ID NO:6.

FIGS. 1A-1C present an alignment of the amino acid sequences set forth in SEQ ID NOs:2, 4, and 6 with the *Helianthus tuberosus* 1-FFT sequence (NCBI General Identifier No. 3367690; SEQ ID NO:17). The alignment indicates with an asterisk (*) above the alignment the amino acids conserved among all the sequences. FIG. 1A shows amino acids 1 through 240, FIG. 1B shows amino acids 241 through 480, and FIG. 1C shows amino acids 481 through 624.

According to van der Meer et al. ((1998) *Plant J.* 15:489-500) the *Helianthus tuberosus* amino acid sequence has a signal sequence corresponding to amino acids 1 through 80. It can be clearly seen from the alignment that the polypeptides having SEQ ID NO:2 and SEQ ID NO:4 contain the conserved domains highlighted by Cha et al. ((2001) *J. Biotech.* 91:49-61) and the conserved Asp and Glu suggested by Saito et al. ((1997) *Biosci. Biotech. Biochem.* 61:2076-2079) as playing a role as nucleophile and proton donor in the catalytic mechanism of fructosyltransferases. In 1-FFTs the "FRDP-F motif" is included within the conserved motif Phe-His-Phe-Gln-Pro-Ala-Lys-Asn-Phe-Ile-Asp-Pro-Xaa-Gly. The "ECPD-R motif" is included within the conserved domain His-Ser-Val-Pro-Asn-Thr-Asp-Met-Trp-Glu-Cys-Val-Asp-Phe-Tyr-Pro-Val-Ser-Leu-Thr-Asn-Asp-Ser-Ala-Leu-Asp. The putative active Asp is included in the first domain and is located at position 95 of both, SEQ ID NO:2 and SEQ ID NO:4. The conserved Glu is found in the second domain, at position 277 of both, SEQ ID NO:2 and SEQ ID NO:4.

The data in Table 4 presents the percent identity of the amino acid sequences set forth in SEQ ID NOs:2, 4, and 6 with the *Helianthus tuberosus* sequence (NCBI General Identifier No. 3367690; SEQ ID NO:17).

TABLE 4

Percent Identity of Amino Acid Sequences Deduced From the Nucleotide Sequences of cDNA Clones Encoding Polypeptides Homologous to 1-FFT

| Clone | SEQ ID NO. | Percent Identity to 3367690 |
|---|---|---|
| dms2c.pk006.p1:fis | 2 | 79.5 |
| epb3c.pk007.j9:fis | 4 | 84.9 |
| hss1c.pk004.i5 | 6 | 86.5 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire African daisy and Guayule 1-FFT and a substantial portion of a sunflower 1-FFT. These sequences represent the first African daisy, guayule, and sunflower sequences encoding 1-FFT known to Applicant.

Example 4

Characterization of cDNA Clones Encoding 6-SFT

The BLASTX search using the EST sequences from clones listed in Table 3 revealed similarity of the polypeptides encoded by the cDNAs to 6-SFT from *Hordeum vulgare* (NCBI General Identifier No. 7435467). Shown in Table 5 are the BLAST results for the sequences of the entire cDNA inserts comprising the indicated cDNA clones ("FIS"):

TABLE 5

BLAST Results for Sequences Encoding Polypeptides Homologous to 6-SFT

| Clone | Status | BLAST pLog Score 7435467 |
|---|---|---|
| wdk1c.pk014.c11 | FIS | >180.00 |
| wdk2c.pk017.f14 | FIS | >180.00 |
| wr1.pk0085.h8 | FIS | 21.30 |

The nucleotide sequence of the entire cDNA insert in clone wdk1c.pk014.c11 is shown in SEQ ID NO:7. The amino acid sequence deduced from nucleotides 3 through 1487 of SEQ ID NO:7 is shown in SEQ ID NO:8. The nucleotide sequence of the entire cDNA insert in clone wdk2c.pk017.f14 is shown in SEQ ID NO:9. The amino acid sequence deduced from nucleotides 1 through 1413 of SEQ ID NO:9 is shown in SEQ ID NO:10. The nucleotide sequence of the entire cDNA insert in clone wr1.pk0085.h8 is shown in SEQ ID NO:11. The amino acid sequence deduced from nucleotides 1 through 174 of SEQ ID NO:11 is shown in SEQ ID NO:12.

The nucleotide sequence encoding the N-terminus for the polypeptide encoded by the cDNA insert in clone wdk2c.pk017.f14 was obtained. The BLASTP search using the amino acid sequence from clones wdk2c.pk017.f14 revealed similarity of the 6-SFT polypeptide from *Hordeum vulgare* (NCBI General Identifier No. 7435467). Shown in Table 6 are the BLAST results for the amino acid sequence of the entire protein encoded by the indicated clone (CGS):

TABLE 6

BLAST Results for Sequences Encoding Polypeptides Homologous to 6-SFT

| Clone | Status | BLAST pLog Score 7435467 |
|---|---|---|
| wdk2c.pk017.f14:cgs | CGS | >180.00 |

A contig of the nucleotide sequence of the entire cDNA insert in clone wdk2c.pk017.f14 and 5'PCR is shown in SEQ ID NO:19. The amino acid sequence deduced from nucleotides 3 through 1916 of SEQ ID NO:19 is shown in SEQ ID NO:20.

FIGS. 2A-2C present an alignment of the amino acid sequences set forth in SEQ ID NOs:8, 10, 12, and 20 with the *Hordeum vulgare* sequence (NCBI General Identifier No. 7435467; SEQ ID NO:21). The alignment indicates with an asterisk (*) above the alignment the amino acids conserved among all the sequences. Dashes are used by the program to maximize the alignment. FIG. 2A shows amino acids 1 through 240, FIG. 2B shows amino acids 241 through 480, and FIG. 2C shows amino acids 481 through 625. It can be clearly seen from the alignment that the polypeptide having SEQ ID NO:20 contains both of the conserved domains mentioned in Example 3 and that SEQ ID NO:8, 10, and 12 only contain the second motif. In 6-SFTs the "FRDP-F motif" is contained within the conserved domain Gln-Thr-Ala-Lys-Asn-Tyr-Met-Ser-Asp-Pro-Asn-Gly-Leu-Met-Tyr which includes the "active Asp" at position 77 of SEQ ID NO:20. In 6-SFTs the "ECPD-R motif" is included within the domain Arg-Thr-Gly-Glu-Trp-Glu-Cys-Ile-Asp-Phe-Tyr-Pro-Val-Gly. The "active Glu" is found at position 158 of SEQ ID NO:8, at position 134 of SEQ ID NO:10, and at position 263 of SEQ ID NO:20.

The data in Table 7 presents the percent identity of the amino acid sequences set forth in SEQ ID NOs:8, 10, 12, and 20 with the *Hordeum vulgare* sequence (NCBI General Identifier No. 7435467; SEQ ID NO:21).

TABLE 7

Percent Identity of Amino Acid Sequences Deduced From the Nucleotide Sequences of cDNA Clones Encoding Polypeptides Homologous to 6-SFT

| Clone | SEQ ID NO. | Percent Identity to 7435467 |
|---|---|---|
| wdk1c.pk014.c11 | 8 | 94.9 |
| wdk2c.pk017.f14 | 10 | 94.7 |
| wr1.pk0085.h8 | 12 | 84.5 |
| wdk2c.pk017.f14:cgs | 20 | 88.7 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode an entire wheat 6-SFTs and substantial portions of a three wheat 6-SFTs. These sequences represent the first wheat sequences encoding 6-SFT known to Applicant.

Example 5

Characterization of cDNA Clones Encoding 1-SST

The BLASTX search using the EST sequences from clones listed in Table 8 revealed similarity of the polypeptides encoded by the cDNAs to 1-SST from *Helianthus tuberosus* (NCBI General Identifier No. 3367711). Shown in Table 7 are the BLAST results for the sequences of the entire cDNA inserts comprising the indicated cDNA clones ("FIS") encoding an entire protein ("CGS"):

TABLE 8

BLAST Results for Sequences Encoding
Polypeptides Homologous to 1-SST

| Clone | Status | BLAST pLog Score NCBI GI No. 3367711 |
|---|---|---|
| epb3c.pk007.n11 | CGS | >180.00 |
| hhs1c.pk004.e5 | CGS | >180.00 |

The nucleotide sequence of the entire cDNA insert in clone epb3c.pk007.n11 is shown in SEQ ID NO:13. The amino acid sequence deduced from nucleotides 42 through 1946 of SEQ ID NO:13 is shown in SEQ ID NO:14. The nucleotide sequence of the entire cDNA insert in clone hhs1c.pk004.e5 is shown in SEQ ID NO:15. The amino acid sequence deduced from nucleotides 59 through 1890 of SEQ ID NO:15 is shown in SEQ ID NO:16.

FIGS. 3A-3B present an alignment of the amino acid sequences set forth in SEQ ID NOs:14 and 16 with the *Helianthus tuberosus* 1-SST sequence (NCBI General Identifier No. 3367711; SEQ ID NO:18). The alignment indicates with an asterisk (*) above the alignment the amino acids conserved among all the sequences. According to van der Meer et al. ((1998) *Plant J.* 15:489-500) the mature *Helianthus* peptide consists of amino acids 100 through 630. FIG. 3A shows amino acids 1 through 350, and FIG. 3B shows amino acids 351 through 637.

It can be clearly seen from the alignment that the polypeptides having SEQ ID NO:14 and SEQ ID NO:16 contain conserved domains which include the motifs mentioned in Example 3. In 1-SSTs the "FRDP-F motif" is contained within the conserved domain Tyr-His-Phe-Gln-Pro-Asp-Lys-Xaa-Ile-Ser-Asp-Pro-Asp-Gly-Pro-Met-Tys-His which includes the "active Asp" at position 115 of SEQ ID NO:14 and at position 108 of SEQ ID NO:16. In 1-SSTs the "ECPD-R motif" is included within the domain Glu-Glu-Val-Leu-His-Ala-Val-Pro-His-Thr-Gly-Met-Trp-Asp-Cys-Val-Asp-Leu-tyr-Pro. The "active Glu" is found at position 293 of SEQ ID NO:8 and at position 286 of SEQ ID NO:20.

The data in Table 9 presents the percent identity of the amino acid sequences set forth in SEQ ID NOs:14 and 16 with the *Helianthus tuberosus* sequence (NCBI General Identifier No. 3367711; SEQ ID NO:18).

TABLE 9

Percent Identity of Amino Acid Sequences
Deduced From the Nucleotide Sequences of cDNA Clones
Encoding Polypeptides Homologous to 1-SST

| Clone | SEQ ID NO. | Percent Identity to 3367711 |
|---|---|---|
| epb3c.pk007.n11 | 14 | 89.2 |
| hhs1c.pk004.e5 | 16 | 96.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire 1-SSTs. These sequences represent the first sunflower and guayule sequences encoding 1-SST known to Applicant.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833-839). Assays for fructosyltransferase activity may be conducted under well known experimental conditions which permit optimal enzymatic activity. For example, assays for 1-FFT and 1-SST are presented by van der Meer et al. (1998) Plant J. 15:489-500. Assays for 6-SFT are presented by Sprenger et al. (1995) Proc. Natl. Acad. Sci. USA 92:11652-11656.

Example 7

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810-812), the hygromycin phosphotransferase gene from plasmid pJR225 (from E. coli; Gritz et al. (1983) Gene 25:179-188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Assays for fructosyltransferase activity may be conducted under well known experimental conditions which permit optimal enzymatic activity. For example, assays for 1-FFT and 1-SST are presented by van der Meer et al. (1998) *Plant J.* 15:489-500. Assays for 6-SFT are presented by Sprenger et al. (1995) *Proc. Natl. Acad. Sci. USA* 92:11652-11656.

Example 8

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 g/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Assays for fructosyltransferase activity may be conducted under well known experimental conditions which permit optimal enzymatic activity. For example, assays for 1-FFT and 1-SST are presented by van der Meer et al. (1998) *Plant J.* 15:489-500. Assays for 6-SFT are presented by Sprenger et al. (1995) *Proc. Natl. Acad. Sci. USA* 92:11652-11656.

What is claimed is:

1. An isolated polynucleotide comprising:
   (a) a nucleotide sequence encoding a polypeptide having 1-FFT activity, wherein the amino acid sequence of the polypeptide and the amino acid sequence of SEQ ID NO:2 have at least 90% sequence identity based on the Clustal alignment method with default parameters of KTUPLE=1, GAP PENALTY=3, WINDOW=5 and DIAGONALS SAVED=5, or
   (b) the complement of the nucleotide sequence, wherein the complement and the nucleotide sequence contain the same number of nucleotides and are 100% complementary.

2. The polynucleotide of claim 1 wherein the amino acid sequence of the polypeptide and the amino acid sequence of SEQ ID NO:2 have at least 95% sequence identity based on the Clustal alignment method with the default parameters.

3. The polynucleotide of claim 1 wherein the polypeptide comprises the amino acid sequence of SEQ ID NO:2.

4. The polynucleotide of claim 1 wherein the nucleotide sequence comprises the nucleotide sequence of SEQ ID NO:1.

5. A vector comprising the polynucleotide of claim 1.

6. A recombinant DNA construct comprising the polynucleotide of claim 1 operably linked to a regulatory sequence.

7. A method for transforming a cell comprising transforming a cell with the polynucleotide of claim 1.

8. A cell comprising the recombinant DNA construct of claim 6.

9. A method for producing a transgenic plant comprising transforming a plant cell with the polynucleotide of claim 1 and regenerating a transgenic plant from the transformed plant cell.

10. A plant comprising the recombinant DNA construct of claim 6.

11. A seed comprising the recombinant DNA construct of claim 6.

* * * * *